(12) United States Patent
Schiff

(10) Patent No.: US 8,694,087 B2
(45) Date of Patent: Apr. 8, 2014

(54) PATIENT CONTROLLED BRAIN REPAIR SYSTEM AND METHOD OF USE

(75) Inventor: Nicholas D. Schiff, New York, NY (US)

(73) Assignee: Cornell University, Ithaca, NY (US)

( * ) Notice: Subject to any disclaimer, the term of this patent is extended or adjusted under 35 U.S.C. 154(b) by 340 days.

(21) Appl. No.: 12/994,427

(22) PCT Filed: May 28, 2009

(86) PCT No.: PCT/US2009/045445
§ 371 (c)(1),
(2), (4) Date: Nov. 23, 2010

(87) PCT Pub. No.: WO2009/146361
PCT Pub. Date: Dec. 3, 2009

(65) Prior Publication Data
US 2011/0106206 A1    May 5, 2011

Related U.S. Application Data

(60) Provisional application No. 61/056,494, filed on May 28, 2008.

(51) Int. Cl.
*A61B 5/0482* (2006.01)
(52) U.S. Cl.
USPC .......................................... 600/545; 600/544
(58) Field of Classification Search
USPC ................................................. 600/544–545
See application file for complete search history.

(56) References Cited

U.S. PATENT DOCUMENTS

| | | | | |
|---|---|---|---|---|
| 5,269,303 | A | * | 12/1993 | Wernicke et al. ............... 607/45 |
| 6,167,298 | A | | 12/2000 | Levin |
| 2004/0015211 | A1 | | 1/2004 | Nurmikko et al. |
| 2004/0267320 | A1 | | 12/2004 | Taylor et al. |

OTHER PUBLICATIONS

PCT International Search Report for PCT/US2009/045445, filed May 28, 2009, completed Jul. 9, 2009.
PCT International Written Opinion for PCT/US2009/045445, filed May 28, 2009, mailed Jul. 21, 2009.

* cited by examiner

*Primary Examiner* — Joseph Stoklosa
(74) *Attorney, Agent, or Firm* — LeClairRyan, a Professional Corporation

(57) ABSTRACT

A method of maintaining an information rate of a Brain-computer interface (BCI) system, implanted in a patient's brain, by regulating arousal level in the patient's brain is disclosed. The method includes selecting a patient with the implanted BCI device configured to receive neuronal activity from one or more electrodes connected to the patient's brain and to establish a communication channel between the patient and an external device controlled by the patient. Accordingly, a rate of information passage through the communication channel from the BCI device is measured, and a region of the patient's brain involved in arousal regulation, is stimulated in response to said measuring, under conditions effective to adjust the rate of information passing from the BCI device through the communication channel. A computer medium for carrying out this method and a BCI Arousal Regulation system are also disclosed.

27 Claims, 19 Drawing Sheets

Combined vascular innervation of thalamus and mesencephalon

Composite of brainstem locations producing coma

PATIENT CONTROLLED BRAIN REPAIR SYSTEM AND METHOD OF USE

This application is a national stage application under 35 U.S.C. §371 of PCT/US2009/045445 filed May 28, 2009, and claims the benefit of U.S. Provisional Patent Application Ser. No. 61/056,494, filed May 28, 2008, each of which is hereby incorporated by reference in its entirety.

FIELD OF THE INVENTION

The present invention generally relates to a patient controlled Brain-Computer Interface system and a method of using the system.

BACKGROUND OF THE INVENTION

Brain-computer interfaces (BCI) represent a large growing area for biomedical device development. One of the goals of BCI devices is to assist patients with severe disabilities. The BCI devices provide direct or indirect reading of neural/neuronal activity through surface or implanted electrodes to obtain at least a 1-bit communication channel under the patient's control. Many brain-injured patients, who have suffered a brainstem stroke, hemorrhage, or axonal injury due to trauma that leads to partial or total paralysis may have injuries to brainstem and forebrain structures that control arousal level. Other patients can have severe damage to motor pathways at higher levels of the brain due a variety of brain insults. Moreover, damage to central motor control structures even without interruption of the motor pathways may produce such severely impaired motor control that clinical distinctions between true damage to motor pathways and motor preparation systems is hard to determine. Most conventional applications of BCI focus on reading in brain activity from a brain-injured subject for providing output to a prosthetic device such as a robot arm or a cursor on a computer screen. However, existing applications of BCI systems do not address the often critical problems of state control for arousal regulation of the forebrain created by the types of brain injuries that produce the need for a BCI. A common problem faced by these patients is a failure to maintain regulation of forebrain neuronal activity within wakeful states corresponding to a base vigilance level (specifically arousal level within the wakeful state) and consequent ability to maintain behavioral sets and complete intended behaviors due to impairment of frontal executive systems that support motor preparation, working memory, sustained attention, and goal-directed action and intentions. In the absence of such a base vigilance/arousal level (e.g., a patient falling back into minimally conscious state where intentions and actions are inconsistent or appear identically inconsistent to patients in minimally conscious state), the conventional BCI devices will fail to operate. In certain situations, such a lapse to a sub-threshold vigilance/arousal level will lead to functional failure of the BCI device. For example, if a patient controlling a prosthetic or an external communication device being operated using a BCI reduces their vigilance level to a point where control of the device is weak or absent, the patient will not be able to communicate or operate external prosthetics that may be controlled by the BCI. In other words, conventional BCI systems fail to link with and utilize the arousal mechanisms of the brain to maintain functional communication with external world through the BCI.

Therefore, there is a need in the current conventional technology to establish a patient-controlled Brain Computer Interface/arousal regulation (BO/AR) system that adapts and accommodates the level of brain activation unique to a patient's use of the BCI to produce an effective communication channel with the outside world, to allow the patient with such problems to reliably and optimally stimulate subcortical regions of the brain and to communicate or control the BCI device itself and/or an external device/prosthetic attached to the BCI.

The present invention is directed to overcoming the above-noted and other deficiencies in the art.

SUMMARY OF THE INVENTION

According to one aspect of the invention, a method of controlling a Brain Computer Interface (BCI) device implanted in a patient's brain is disclosed herein. The method comprises selecting a patient with the implanted BCI device configured to receive neuronal activity from one or more electrodes connected to the patient's brain and to establish a communication channel between the patient and an external device controlled by the patient. A rate of information passage through the communication channel from the BCI device is measured, and a region of the patient's brain involved in arousal regulation is stimulated, in response to the measuring, under conditions effective to adjust the rate of information passing from the BCI device through the communication channel.

Another aspect of the present invention is directed to a computer readable medium having stored thereon instructions for controlling a Brain Computer Interface (BCI) device implanted in a selected patient's brain. The computer readable medium comprises machine executable code which when executed by at least one processor, causes the processor to perform a series of steps. Neuronal activity received from one or more electrodes is detected at a Brain Computer Interface (BCI) device attached to the selected patient's brain. A communication channel is established between the patient and an external device controlled by the patient. A rate of information passing through the communication channel from the BCI device is measured. A region of the patient's brain involved in arousal regulation is stimulated, in response to the measuring, under conditions effective to adjust the rate of information passing from the BCI device through the communication channel.

Another aspect of the present invention is a Brain Computer Interface (BCI) system that includes one or more sensors configured to detect neuronal activity of one or more cortical or subcortical neuronal populations involved in arousal regulation of a selected patient's brain. A state monitoring module is coupled to the one or more sensors, and is configured to store and process a first set of variables associated with a state of the detected neuronal activity. A performance monitoring module is coupled to the one or more sensors, and is configured to store and process a second set of variables associated with an information rate of the detected neuronal activity. The performance monitoring module is also configured to output the information to an output device via a communications channel. A processing module is coupled to the state monitoring module and the performance monitoring module, and is configured to extract a feature vector based upon the processed first and second set of variables. The processing module is configured to stimulate, in response to the detected neuronal activity, a region of the patient's brain involved in arousal regulation under conditions effective to adjust the information from the BCI device through the communication channel.

Various embodiments of the present invention are disclosed to aid patients with virtually extinct motor pathways or dysfunctional executive control systems to maintain forebrain neuronal activity within wakeful states corresponding to base vigilance levels (specifically basal arousal levels within a wakeful state) by using optimal feedback to cortical or subcortical tissues, and corresponding neuronal populations, of the brain. For example, some patients with marked fluctuations in vigilance/arousal level will have only limited time periods during which they may be able to control a BCI device. For example, if a patient controlling a prosthetic or an external communication device being operated using a BCI reduces their vigilance level to a point where control of the device is weak or absent they will lose the capacity to communicate important needs such as pain control, hunger, thirst or other immediate or more long-range needs. Similarly, patients using BCI devices to operate external prosthetics such as robotic arms, computers, or switches that may be controlled by the BCI will lose or degrade their capacity to optimally control such devices due to fluctuations in vigilance/arousal. The present invention aims to overcome these limitations of conventional BCI systems which fail to link with and utilize the arousal mechanisms of the brain to maintain functional communication with external world through the BCI.

DETAILED DESCRIPTION OF THE INVENTION

Figure 1:
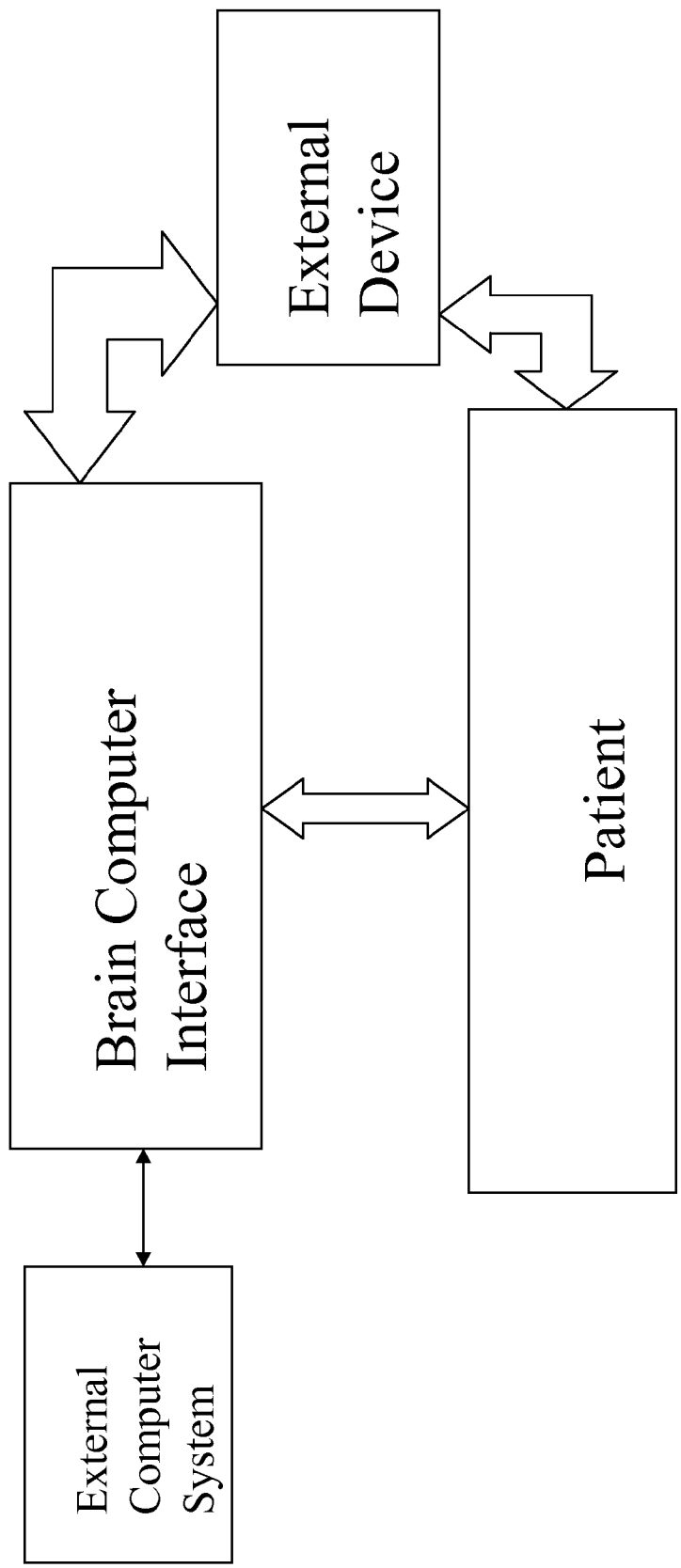
FIG. 1 illustrates an exemplary environment where a patient whose motor pathways are damaged using a BCI device for arousal regulation and operation of an external device, according to one embodiment of the present invention.

FIG. 1 illustrates a patient affected by brain damage using a Brain Computer Interface (BCI) system to optimize a BCI function, such as rate of information passage, by maintaining and regulating arousal levels and optionally control an external device such as a robotic arm using neuronal activity patterns detected by the BCI device. Such an external device can be connected to the BCI device, and/or optionally to the patient's body. In many situations, such a patient cannot control the BCI device to produce external communication triggers due to a temporary or permanent damage to his/her arousal pathways. As a result, control of the BCI device is effortful and many patients attempting to use such "thought control" methods describe fatigue from this effort. In such situations, using the BCI/AR device of the present invention, the patient can be kept at a threshold level/state of arousal or vigilance. For example, the patient's brain arousal level can be elevated within a wakeful state (or awoken from a drowsy state), if and when the BCI/AR monitored information drops below a specified level or separately monitored cortical or sub-cortical neuronal activity falls below a pre-determined value. This is adjusted by sending a stimulation pulse of specific intensity and frequency to the cortical or sub-cortical structures in the patient's brain involved in arousal regulation. Alternatively, the patient's neuronal activity from various regions within the brain can be detected and used to control a robotic arm to feed the patient. Using such a internal neuronal activity determined control, the patient can attain substantial level of independence in taking care of himself/herself, and communicate with the external world. In yet another example, the patient can perform other activities of daily living such as self-administering medications, operating a remote control for a television or operating an automated wheelchair to move to a desired location using internally generated neuronal activity patterns, while at the same time maintaining basal arousal levels by timely administering optimal stimulation pulses to appropriate regions of the brain.

Figure 2A:
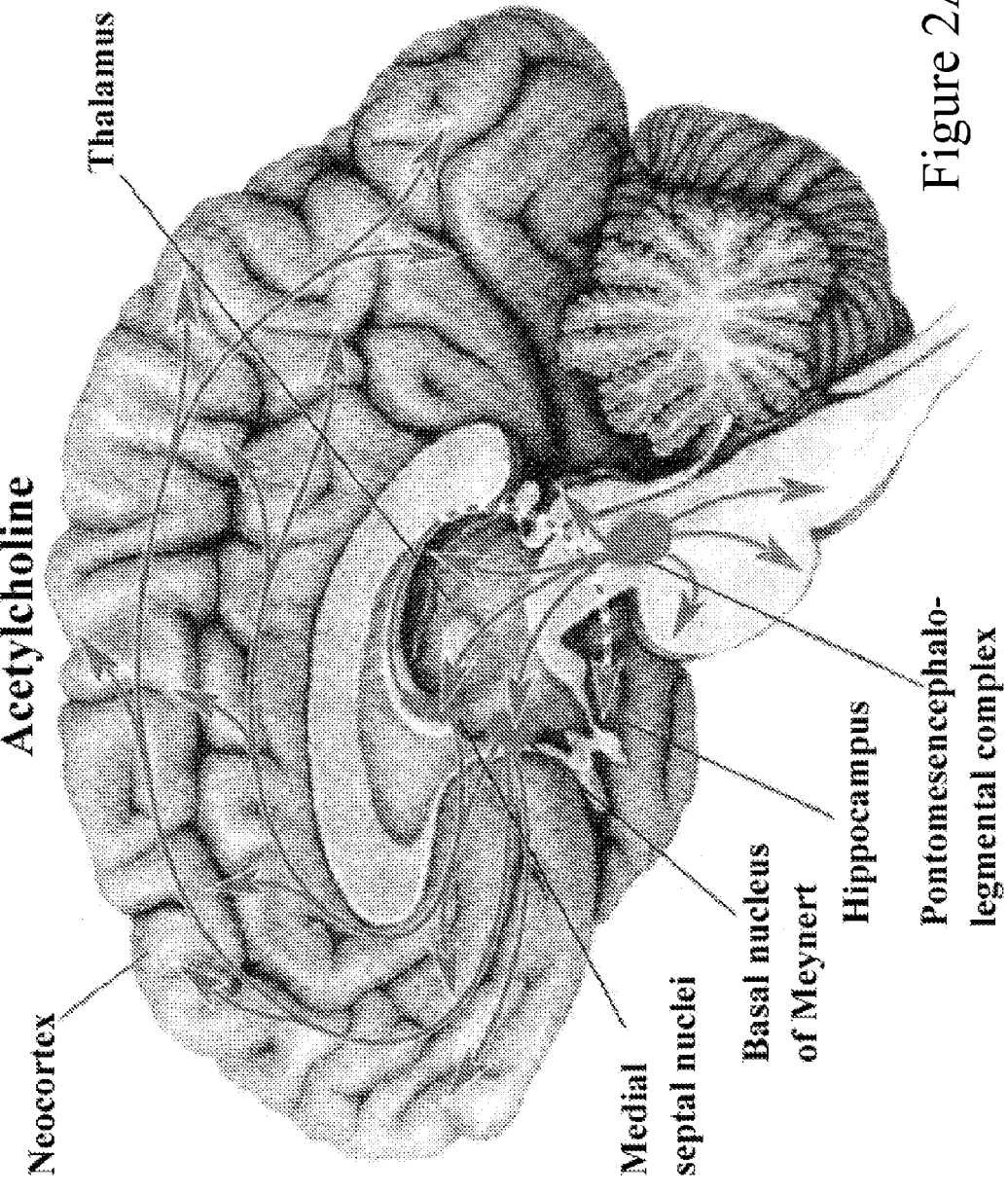
FIGS. 2A-2D illustrate various components of a brain's arousal mechanism.

FIGS. 2A-2D illustrate various exemplary arousal pathways of a brain. For example, FIG. 2A illustrates the cholinergic component of the patient's arousal system showing pathways for neuronal signals originating from the pontomesencephalon outwardly towards basal nuclei, septal nuclei and other regions of the brain. Such neuronal activity pathways are well known to those skilled in the art.

Figure 2B:
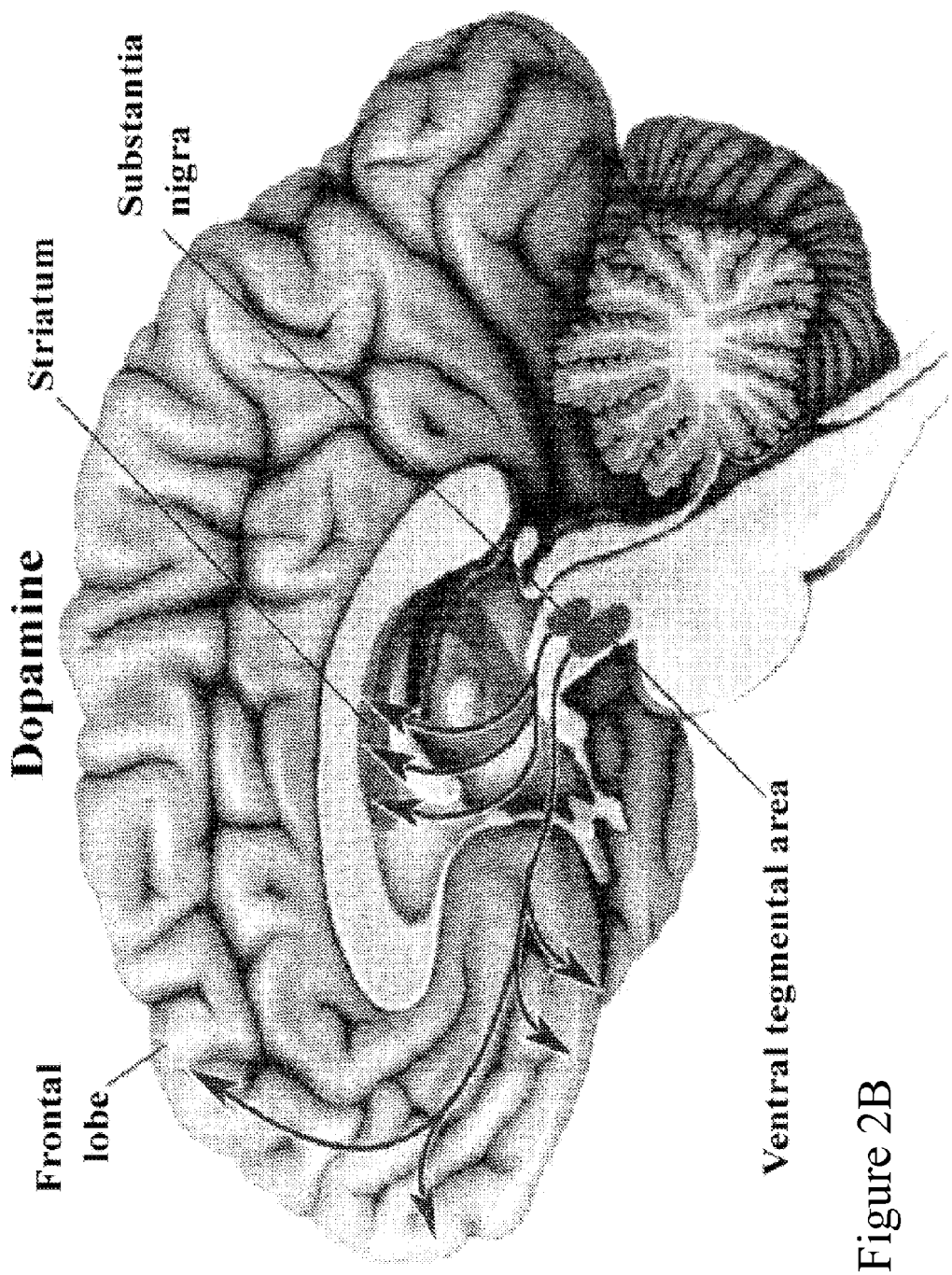

FIG. 2B illustrates the dopaminergic component of the patient's arousal system showing pathways for neuronal signals originating from the ventral tegmental area and the substantia nigra outwardly towards the frontal lobe, striatum, and other regions of the brain. Such neuronal activity pathways are well known to those skilled in the art.

Figure 2C:
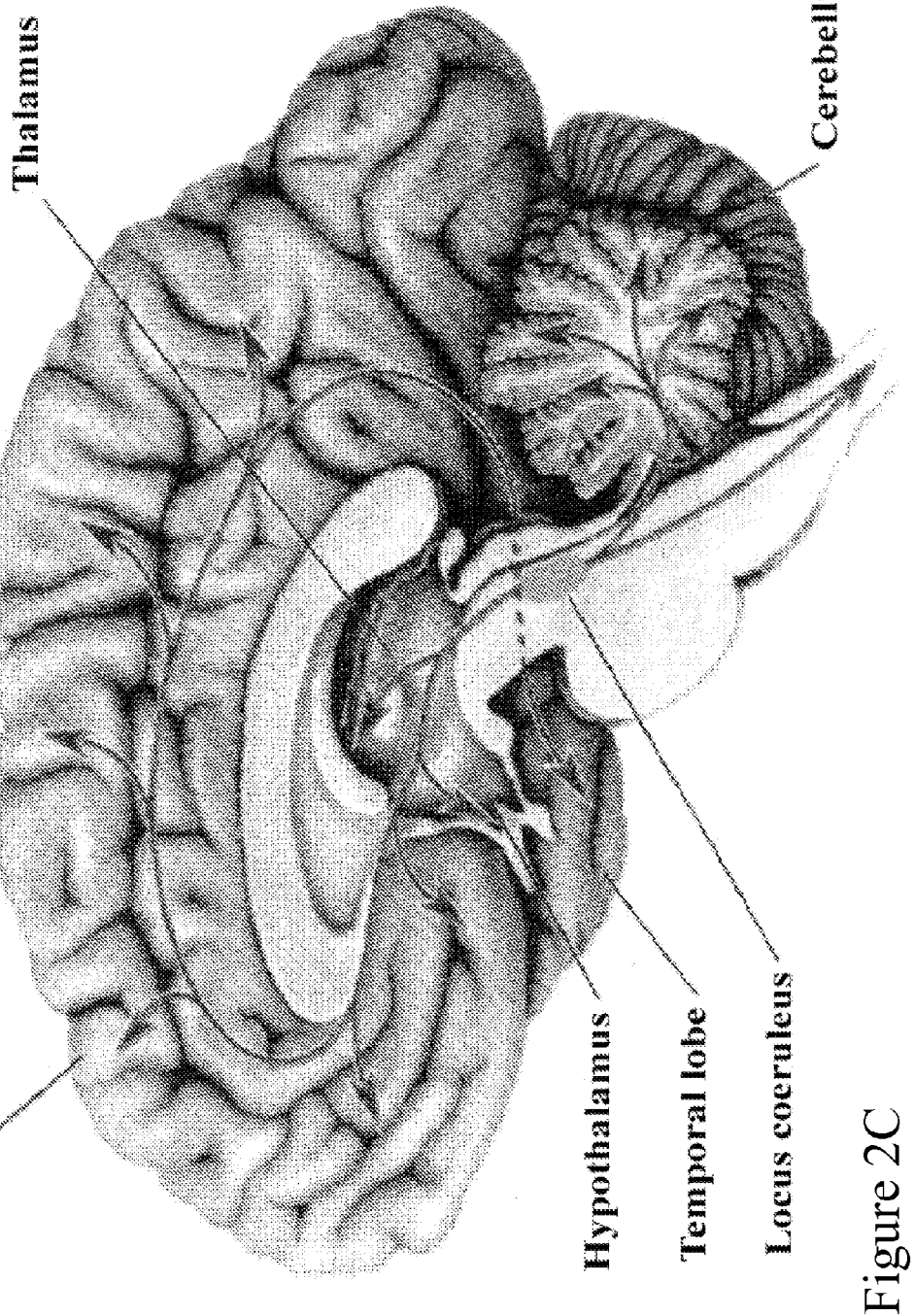

FIG. 2C illustrates the noradrenergic component of the patient's arousal system showing pathways for neuronal signals originating from the loceus coeruleus outwardly towards the temporal lobe, cerebellum, spinal cord, thalamus, hypothalamus, neocortex, and other regions of the brain. Such neuronal activity pathways are well known to those skilled in the art.

Figure 2D:
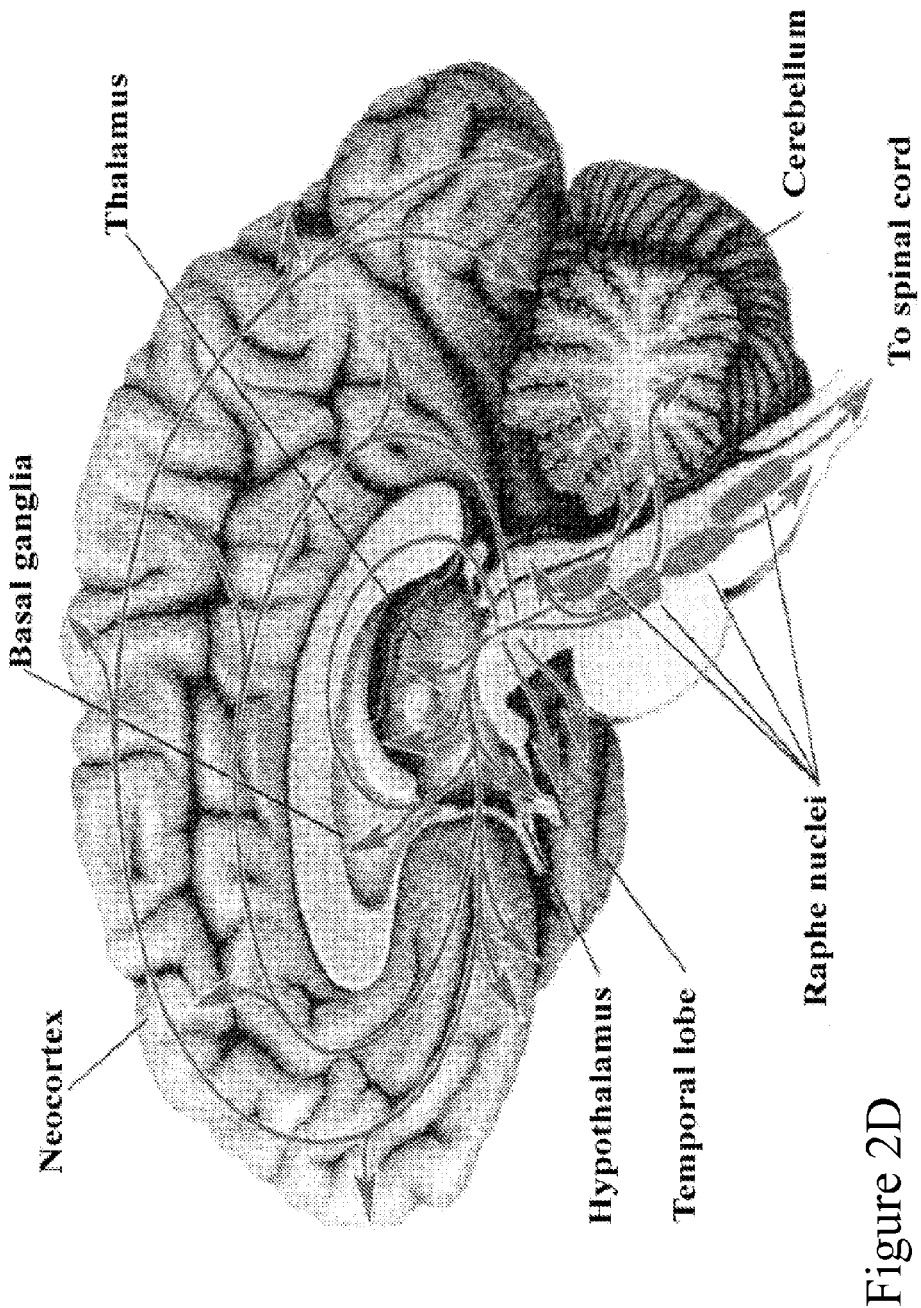

FIG. 2D illustrates the serotinergic component of the patient's arousal system showing pathways for neuronal signals originating from the Raphe nuclei outwardly towards the basal ganglia, temporal lobe, hypothalamus, cerebellum, spinal cord, neocortex, and other regions of the brain. Such neuronal activity pathways are well known to those skilled in the art.

Figure 3B:
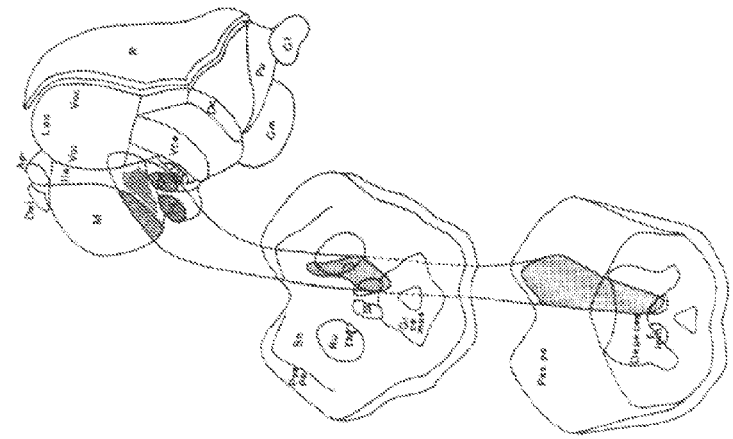
FIG. 3B illustrates combined vascular innervation of the thalamus and mesencephalon.
Figure 3A:
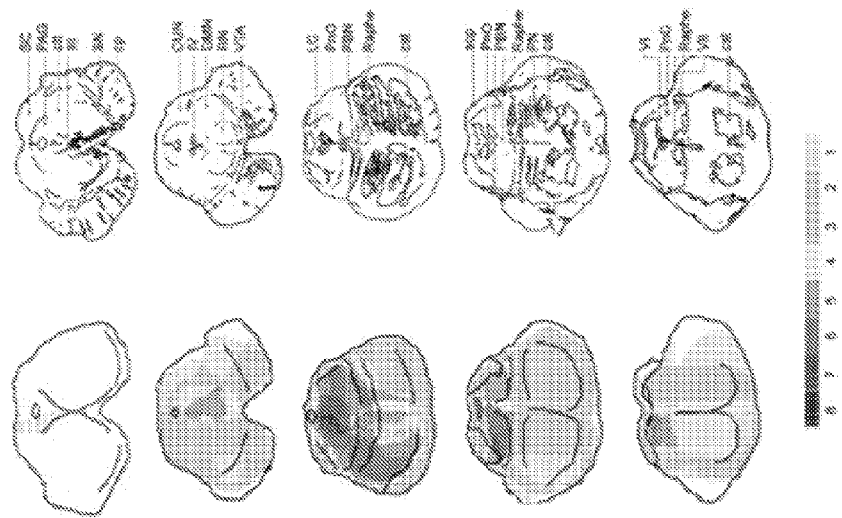
FIG. 3A illustrates a composite of brainstem locations producing coma when lesioned.
Figure 3C:
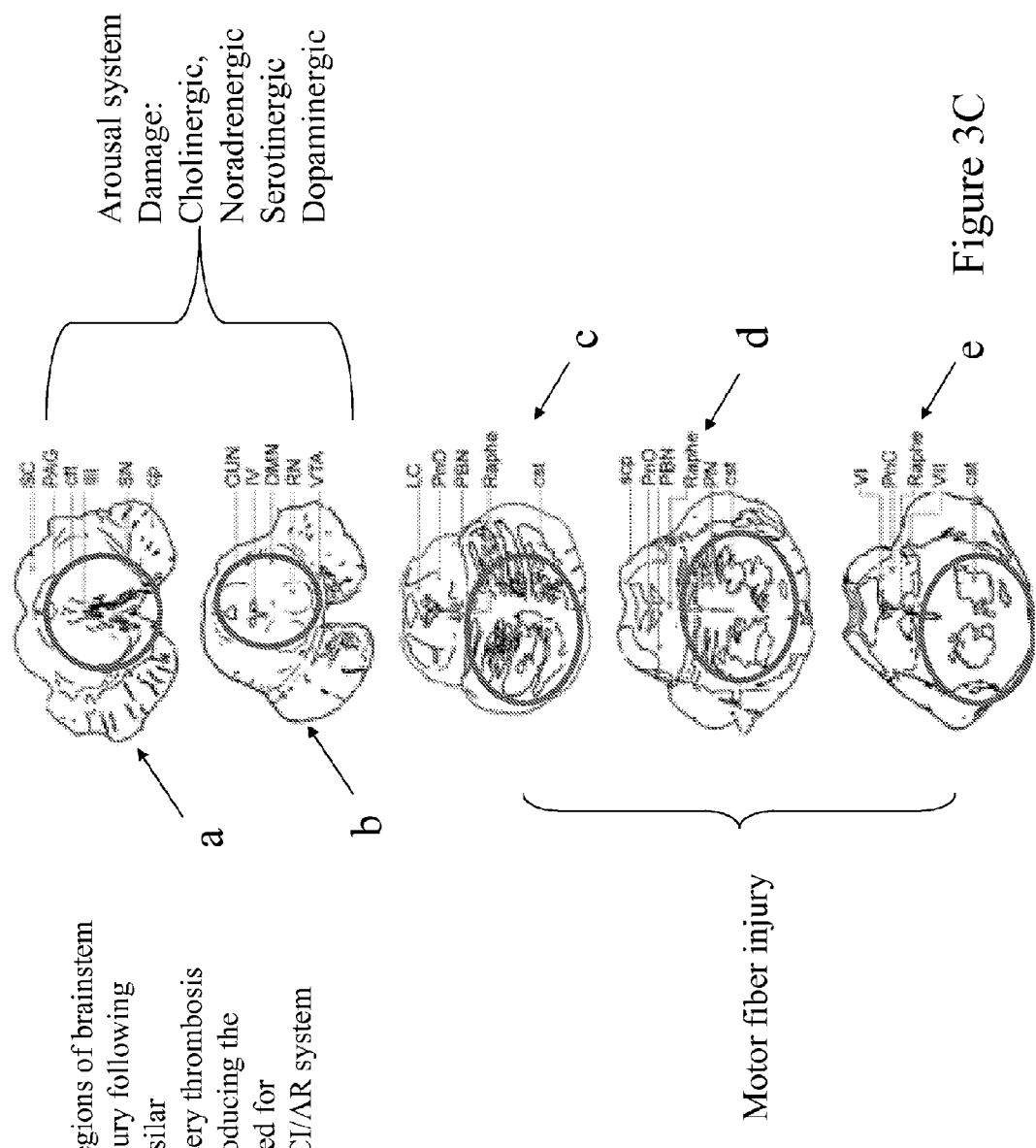
FIG. 3C illustrates various regions of brainstem injury following basilar artery thrombosis where a BCI arousal regulation (AR) system can be utilized.

Although FIGS. 2A-2D illustrate only four different components of a brain's arousal systems, the present invention can equally be used for other arousal system components of a brain known to one skilled in the art. Additional exemplary scenarios where the present invention can be utilized are illustrated in FIGS. 3A-C. FIG. 3A illustrates a scenario where damage to a composite of brainstem locations has initially led to a patient being in a coma or a "vegetative state" but has recovered consciousness with inconsistent capacity to control motor output. Such locations have been described, for example, in Parvisi et al., "Neuroanatomical Correlates of Brainstem Coma," *Brain,* 126(Pt 7):1524-36 (2003), which is hereby incorporated by reference in its entirety. In such a scenario, the patient of FIG. 1 is unable to take any care of himself/herself at all. However, the patient's brain shows anatomical and electrical activity resulting from firing of neurons (neuronal activity) consistent with preservation of large-scale integrative brain function and the capacity to communicate. According to one embodiment of the present invention, brain electrical activity can be detected by an electrical detector attached to a BCI device, recorded in a memory or other computer readable media of a computer system, and analyzed for extracting information relating to, for example, level of activity. Such an analyzed signal can then be used to generate a response stimulus signal, using, for example, an implantable pulse generator, to send an appropriate optimal electrical activation to subcortical structures in the brain involved in forebrain arousal. Such a feedback can result in triggering of one or more of the arousal mechanisms, such as those described in FIGS. 2A-2D, thereby resulting in a wakeful "aroused" state of the patient. Alternatively, by way of example and not as a limitation, other forms of detection and stimulation, such as sampled local field potential recordings coupled to a fiber-optogenic system or a radio-frequency controlled "BION" system can be used.

FIG. 3B illustrates another exemplary scenario of brain injuries produced by loss of blood flow in a specific vascular innervation producing neurological conditions for which the present invention can be applied. Such scenarios are described, for example, by Castaigne et al., "Paramedian Thalamic and Midbrain Infarct: Clinical and Neuropathological Study," *Ann. Neurol.,* 10(2):127-48 (1981), which is hereby incorporated by reference in its entirety.

FIG. 3C illustrates yet another exemplary scenario where a patient has suffered a complete basilar artery thrombosis leading to a substantial damage to motor pathways. For example, in slides a and b, circled areas of FIG. 3C show damage to the various components of the arousal system. Alternatively, in slides c-e, circled areas illustrate motor fiber injury. Such damage scenarios are well known to one skilled in the art.

As a result of the above-noted damage to various regions of the brain, the patient is unable to respond to external stimuli and requires a personal care assistant to help him/her with day to day activities. However, the entirety of the patient's forebrain remains intact, neuronal activity resulting from the patient's thought or desire to express a motor gesture can be measured using the BCI device to read electrical or other forms of electromagnetic signals and send a corresponding control signal to a prosthetic device to be set in motion. Such a prosthetic device can be, for example, a robotic arm optionally attached to a patient's body. Alternatively, such a robotic arm can be attached to a controller to be moved based upon the signal from the BCI device.

Although many patients with brain-injuries might be helped by such a technology (e.g., those with post head injury, encephalitis, subarachnoid hemorrhage, and cardiac arrest/hypoxic ischemic encephalopathy with resulting dysfunction of the basal ganglia, or other injuries), one large group of patients typically requiring this type of combined BCI/AR system are those who have survived a basilar artery thrombosis (described above in FIG. 3C, slides a and b). This lesion and similar forms of injury such as hemorrhages or infections within the upper brainstem may produce a combination of ventral pontine damage in association with injury to the tegmental pons and midbrain regions damaging ascending arousal projections to the thalamus and basal forebrain. Often these latter injuries include damage to the thalamic intralaminar system that supports activation of the frontal executive and basal ganglia systems. As a result of such injuries, patients may slowly recover to an unstable wakeful state of consciousness, retaining normal or near-normal cognitive function that is fragile in the face of mild inter-current stress (sleep deprivation, infection, etc). When combined with injury to the ventral pons that damages the majority of descending motor pathways, it may be nearly impossible or impossible for these patients to signal response through the motor system. Often such patients will be inappropriately diagnosed as in vegetative or minimally conscious state although they have close to normal function. The present invention provides a method of maintaining internal levels of arousal through the patient's own brain controlled adjustment of activity level via a BCI/AR system that both controls the activation of subcortical systems downregulated by loss of ascending inputs and use of the same system to control communication with the outside world and external devices such as motor prosthetics.

Other scenarios where a patient can be selected for treatment using the present invention include a patient with deficiencies in vigilance, motor pathway impairment, motor control impairment, lack of arousal maintenance, brain injury due to stroke, brain injury to due to trauma, encephalitis, subarachnoid hemorrhage, brain stem hemorrhage, brain stem infection, basilar artery thrombosis, thrombosis cardiac arrest, hypoxia, nutritional deficiencies, degenerative illness, neoplastic diseases, infectious diseases, or complications thereof.

Figure 4:
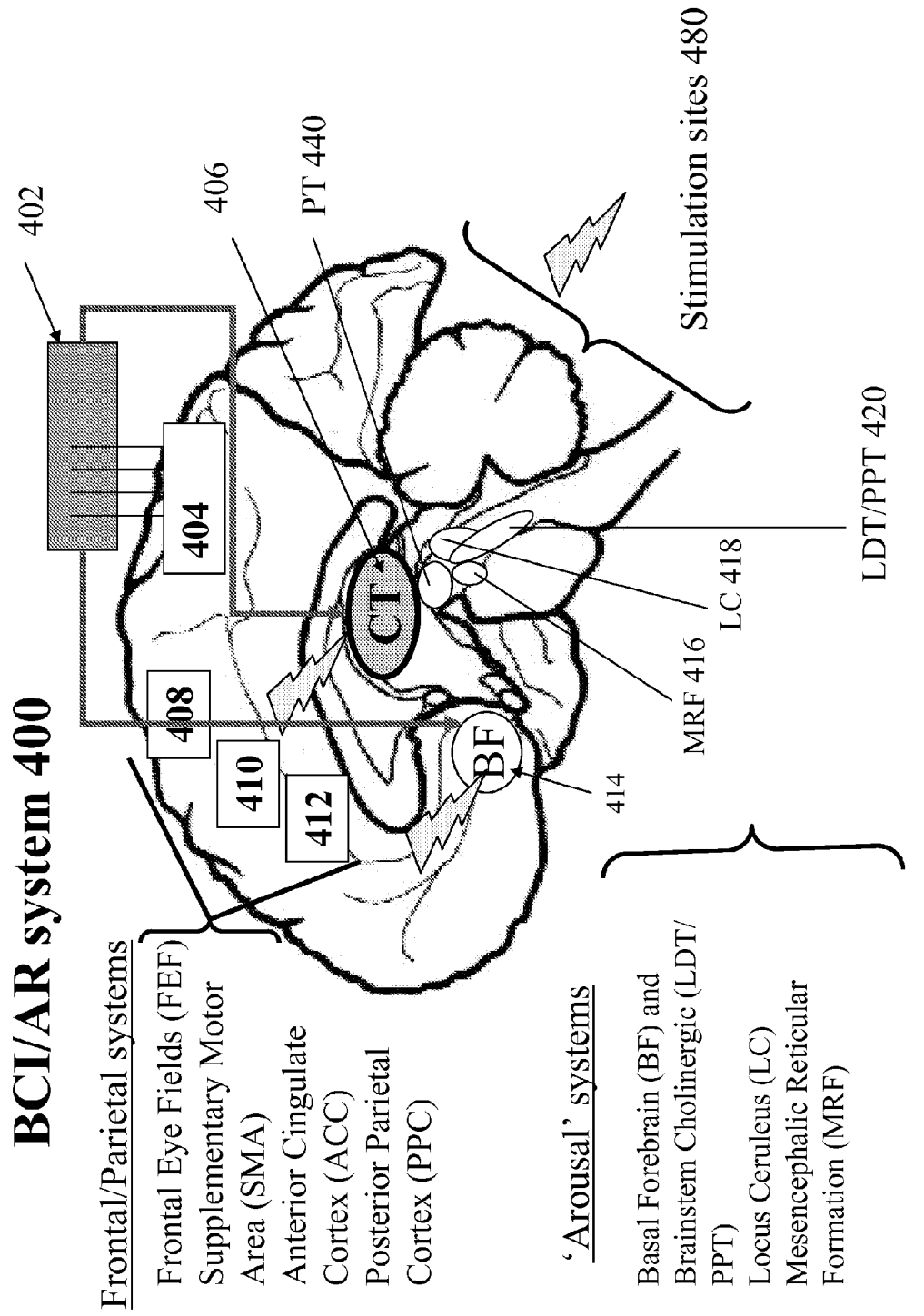
FIG. 4 illustrates exemplary locations where a BCI system can be targeted and corresponding arousal systems of the brain.

FIG. 4 illustrates exemplary locations and arrangement where a BCI/AR system 400 can be used. The main targets of BCI/AR system 400 that control level of arousal above the brainstem level are the basal forebrain and thalamus, the basal ganglia are also innervated by these systems and their role in motor control is strongly affected by brainstem lesions. A traditional BCI system (local field or spike detection systems), such as BCI/AR system 400, situated in the posterior cortical regions such as that described by Andersen et al., "Cognitive Neural Prosthetics," *Trends in Cognitive Sci.,* 8(11):486-93 (2004), which is hereby incorporated by reference in its entirety, can be an exemplary site for cortical read in and read out since the post-rolandic regions of the cerebral cortex do not have the grey matter structures of the basal ganglia interposed between the cortex and thalamus. However, these pathways are very sensitive to brain injuries and can be shut down during the wakeful state producing impaired motor control. As a result, conventional BCI systems will fail to reliably operate when a patient is in a wakeful state but has an impaired motor control. Conventional BCI/AR system 400 comprises a BCI/AR device 402 located at an exemplary region of the brain. BCI/AR system 402 is also connected to Central Thalamus 406 via a communication system to detect neuronal activity and stimulate this structure. FIG. 4 shows regions of the brain corresponding to Frontal Eye Fields (FEF 408), supplementary Motor Area (SMA 410), Anterior Cingulate Complex (ACC 412), and Posterior Parietal Cortex (PPC 404) from which electrical activity resulting from firing of neurons can be detected and sent to controller 402 for further processing for use either in detecting signal used to decode information or sample background brain activity to measure arousal state. FIG. 4 also shows exemplary various sites of the brain such as Basal Forebrain (BF 414), Brainstem Cholinergic (LDT/PPT 420), Locus Ceruleus (LC 418), Mesencephalic Reticular Formation (MRF 416), pretectum PT 440, along with some other stimulation sites 480 (e.g., basal ganglia) from which neuronal activity can be detected.

Another aspect of the present invention is a Brain Computer Interface (BCI) system that includes one or more sensors configured to detect neuronal activity of one or more cortical or sub-cortical neuronal populations involved in arousal regulation of a selected patient's brain. A state monitoring module is coupled to the one or more sensors, and is configured to store and process a first set of variables associated with a state of the detected neuronal activity. A performance monitoring module is coupled to the one or more sensors, and is configured to store and process a second set of variables associated with an information rate of the detected neuronal activity. The performance monitoring module is also configured to output the information to an output device via a communications channel. A processing module is coupled to the state monitoring module and the performance monitoring module, and is configured to extract a feature vector based upon the processed first and second set of variables. The processing module is configured to stimulate, in response to the detected neuronal activity, a region of the patient's brain involved in arousal regulation under conditions effective to adjust the information from the BCI device through the communication channel.

Figure 5:
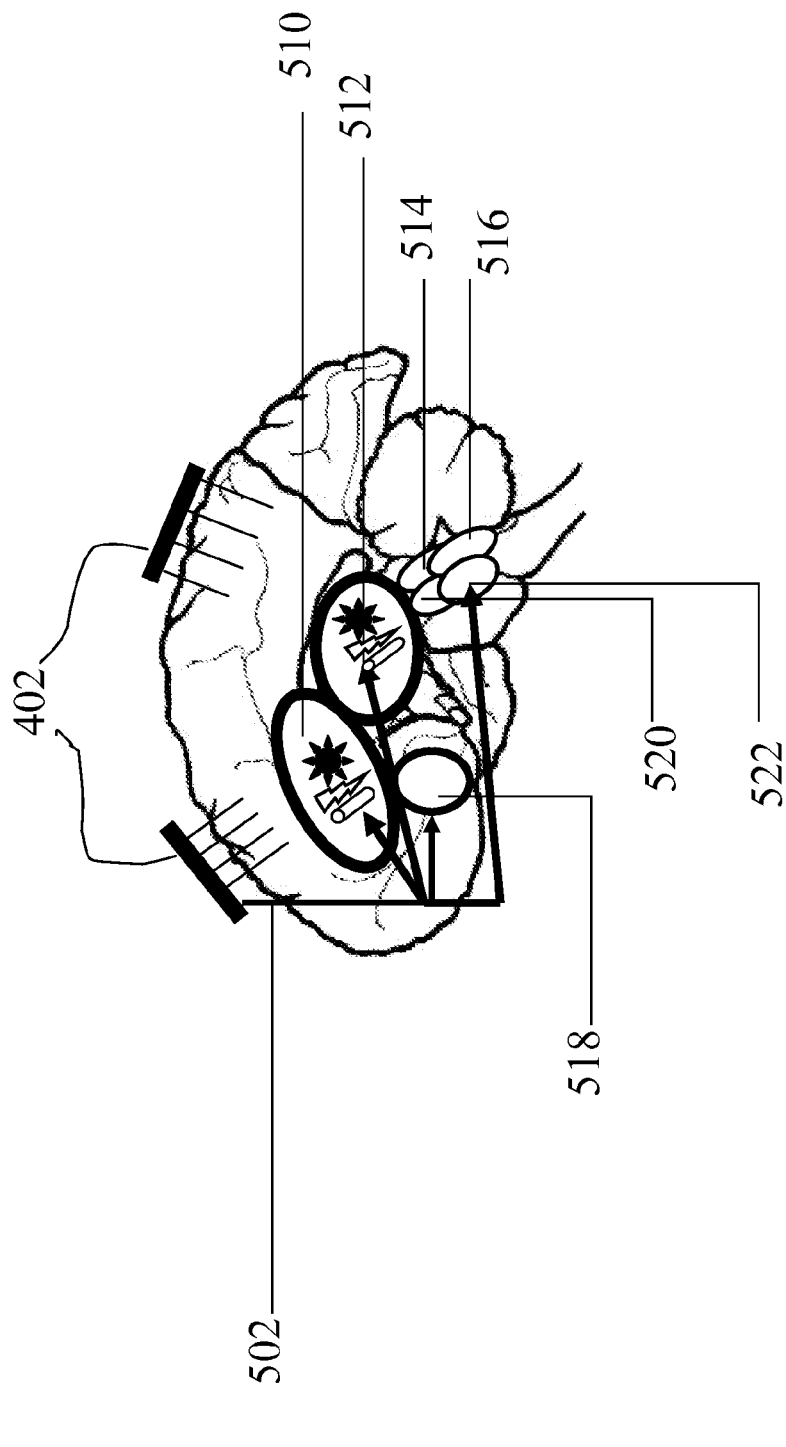
FIG. 5 illustrates an exemplary setup of a BCI-AR system and device, according to an embodiment of the present invention.

FIG. 5 illustrates an exemplary setup of such a brain-computer interface/arousal regulation (BCI/AR) system 500 according to one embodiment of the present invention. The BCI/AR system 500 comprises BCI/AR device 402 including a cortical readout system that collects and stores neuronal data in the form of single-unit activity, local field potentials, or electrocorticogram activity. Connections 502 from BCI/AR device 402 can be electrical, electromagnetic (wireless), or optical to one or many subcortical targets to be determined by availability and involvement in specific patterns of brain injury. The subcortical targets for modulation using, such as electrical brain stimulation methods and systems using an electrical stimulator 506, a fiber-optic/optogenetic system 508, or radiofrequency controlled "BION" system 504, include various regions of the brain, such as the central thalamus, striatum, basal forebrain and brainstem (shown in FIG. 5 as elements 510-522).

Figure 6:
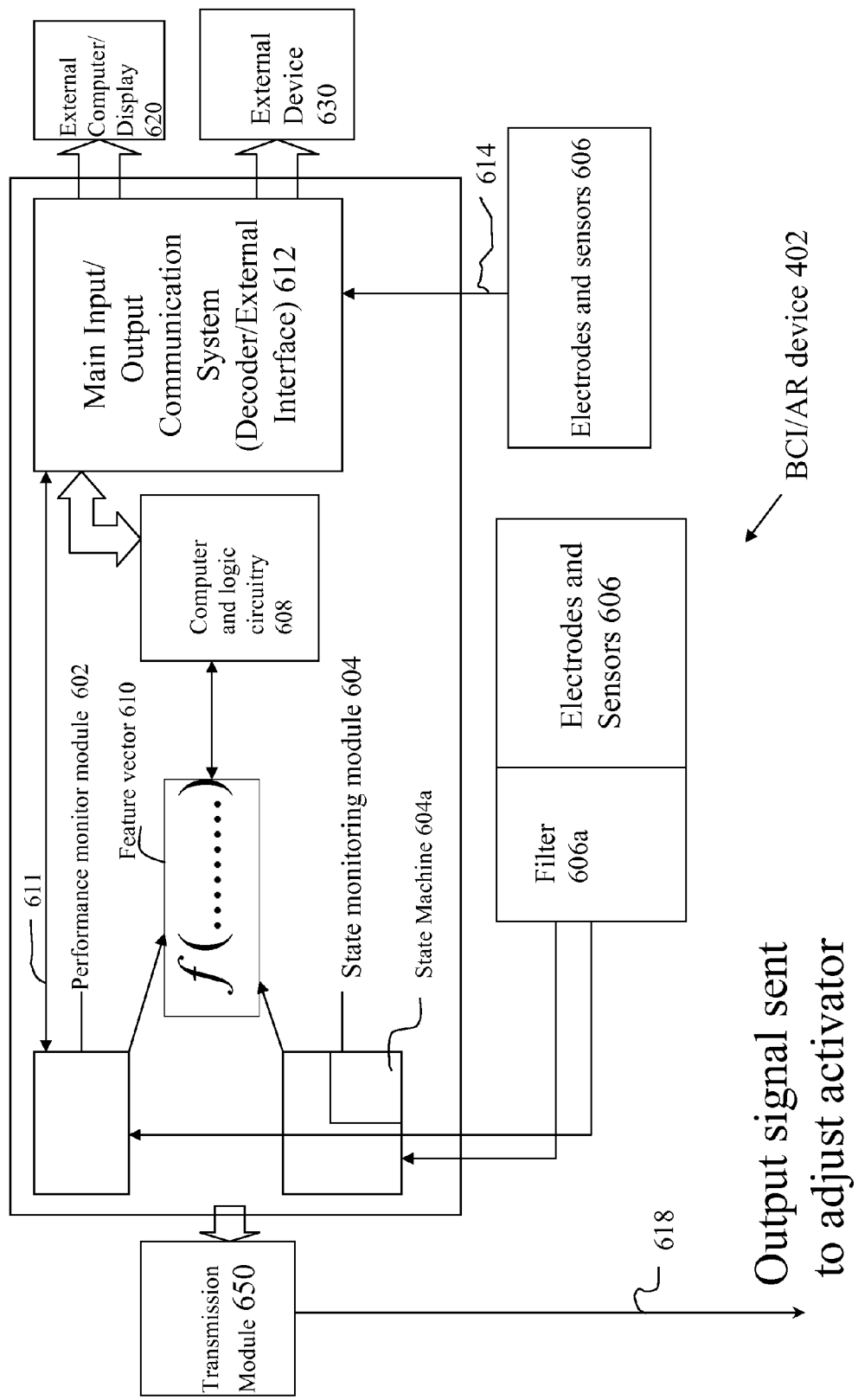
FIG. 6 illustrates an exemplary schematic showing details of the BCI device, according to another embodiment of the present invention.

FIG. 6 illustrates an exemplary internal schematic of BCI/AR device 402 illustrated in FIG. 4 modified according to various embodiments of the present invention. References hereinafter to BCI/AR device 402 are meant to be for the modified BCI/AR device 402 of FIG. 6. BCI/AR device 402 has an internal structure that, in addition to a main input/output interface 612 is designed to decode neuronal signals and translate them into informative outputs that allow for establishing a communication system. BCI/AR device 402 contains a first performance monitoring module 602 used to monitor the performance characteristics of main input/output system 612 (e.g., average bit rate over time, or bit rate in response to specific internally generated probe programs used to train both the patient and BCI/AR system 500 at time of initialization of the device). First performance monitoring module 602 is in direct communication with main input/output system 612, as shown by link 611. A second state monitoring module 604 is used to sample the average characteristics of neuronal activity over time from BCI electrodes and sensors 606 themselves or implanted detectors inside or outside of the brain that collect neuronal signals for this purpose and to provide feedback the real-time characteristics of the signals to BO/AR system 500, and to receive adjusted stimulation signals from BCI/AR device 402. Both of these monitoring modules can communicate with an internal memory and computational resources (described in FIG. 10) to extract signal features such as spike rate or spectral characteristics of the neuronal signal.

Second state monitoring system 604 configured to monitor the state of BCI/AR device 402 in terms of background noise, low-pass filtering, electrocorticogram/electroencephalogram activity, and single-unit firing rates of neurons. Second state monitoring system 604 maintains a state machine 604*a* configured to store various variables related to a state of the neuronal activity at various time points during operation of BO/AR device 402.

Based upon respective sets of variables stored and/or measured, performance monitoring module 602 and state monitoring module 604 are used to extract a feature vector 610 from the variables using computer and logic circuitry 608. Feature vector 610 represents a complete mathematical description of electrical signals resulting from neuronal activity. Such a computed feature vector 610 can be used for further processing and to synthesize a feedback signal if necessary, as described below. Feature vector 610 can also be used to calculate an intensity level of the feedback stimulus signal sent to the subcortical tissues of the brain via an external activation device/system (shown in FIGS. 7-9) connected to BCI/AR device 402 to optimize an output bit-rate of main input/output system 612. Such a feedback signal can be outputted via an electrical path 618. Alternatively, electrical path 618 can use optical, radio frequency, or other frequencies of the electromagnetic spectrum known to one skilled in the art. A separate component of BCI/AR system 500 computes an output signal to the activator units placed in cortical or sub-cortical structures to regulate their output in response to ongoing analysis provided by the two internal monitoring systems 602 and 604.

BCI/AR device 402 detects neuronal activity in the basal ganglia and other regions of the brain using electrodes and sensors 606. Electrodes and sensors 606 can be configured to detect direct electrical activity of neurons, or can be configured to detect neuronal activity converted to optical signals and transmitted using fiber optics. Alternatively, detected neuronal activity can be directly sent via input-output interface 612 (also referred to as I/O interface 612) of BCI/AR device 402 to an external display of an external computer system 640 for inspection by a medical professional or a doctor.

According to one embodiment of the system, computer and logic circuitry 608 can interface with input-output communication interface 612, to control an external device 630, such as a prosthetic arm, via communication path 620, based upon neuronal activity of the patient. Input-output interface 612 can also comprise a direct interface 614 from electrodes and sensors 606 and accordingly can be used for controlling external device 630, for example, when BCI/AR device 402 is operating at an optimal performance range 1302 (shown in FIG. 13).

Although computer and logic circuitry 608 is shown in FIG. 6 to be inside BCI/AR device 402, computer and logic circuitry 608 can optionally be outside BCI/AR device 402 or can be a part of a distributed computing environment too, depending upon specific applications. Further, BCI/AR device 402 can be powered, for example, by batteries or direct mains, or other powering schemes known to one skilled in the art.

Figure 7:
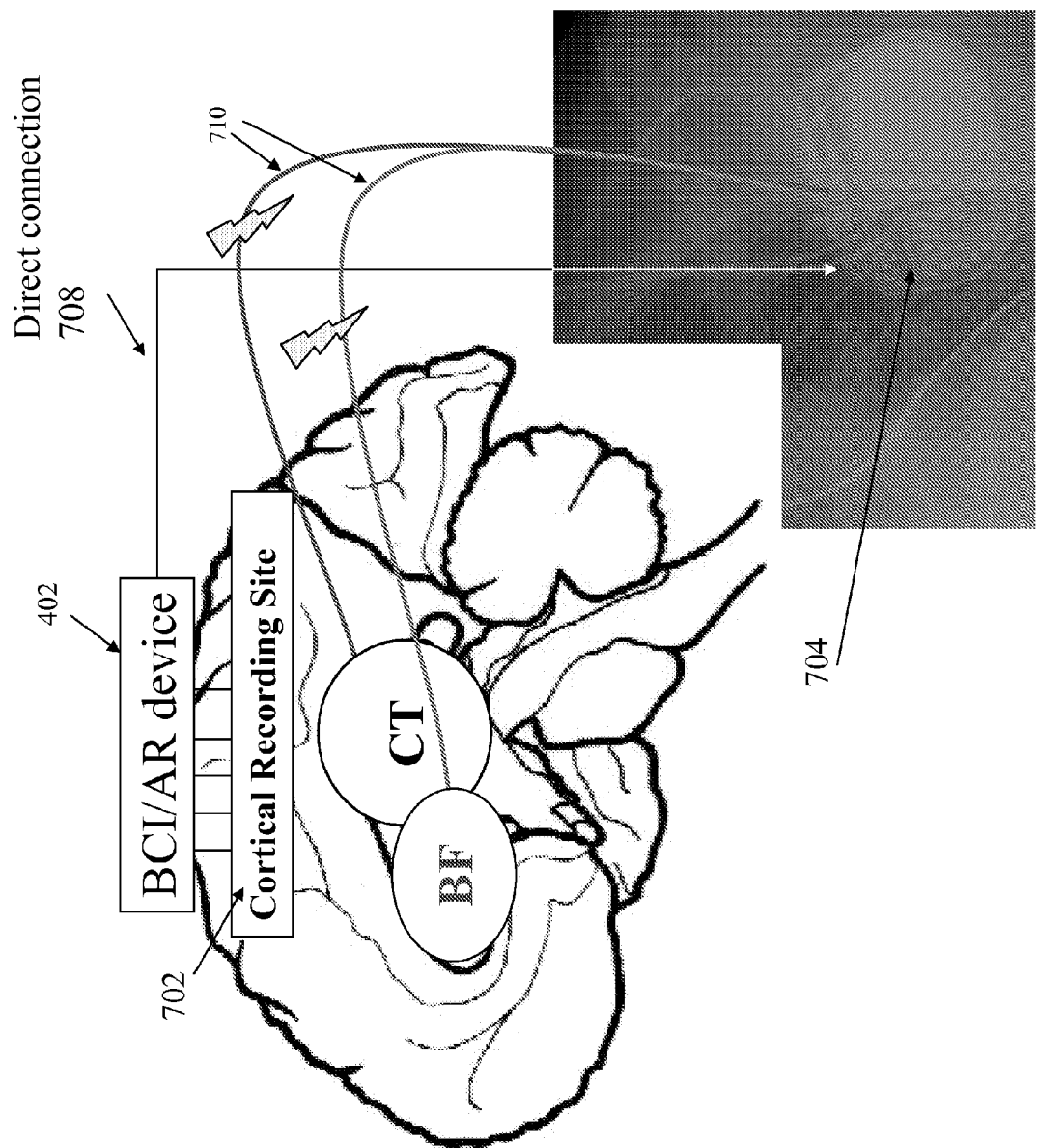
FIG. 7 illustrates a BCI-AR device with an electrical stimulator implanted inside the brain, according to another embodiment of the present invention.

FIG. 7 illustrates one embodiment of the present invention where BCI/AR device 402 is interfaced directly to a conventional implantable pulse generator 704. Implantable pulse generator 704 is configured to feedback control of electrical stimulation of exemplary subcortical targets such as basal forebrain (BF) and central thalamus (CT) via electrical leads 710. Upon receipt of a signal via connection 708, implantable pulse generator 704 can provide a corresponding stimulus to the BF and CT regions of the brain via electrical leads 710 to maintain the arousal state of a patient.

FIG. 7 also shows a cortical recording site 702 (also referred to as neuronal recording system) coupled to BCI/AR device 402. Cortical recording site 702 samples various information such as electrical waveform pattern data unique to the patient. Further, BCI/AR device 402 performs storage in real time when cortical recording site 702 samples electrical activity, and also can be used to retrieve signals stored during an off-line operation. Cortical recording site 702 can also be configured to obtain information related either to obtaining a 'one-bit' communication signal or the background arousal level of the brain.

Cortical recording site 702 is introduced under the skull and either sits on the brain or is inserted into the brain parenchyma and connects to one or multiple probes/leads 710, via BCI/AR device 402, implanted within the brain. BCI/AR device 402 detects the occurrence of failures of human control and adjusts stimulation of subcortical targets in synchrony, as described above. The operating characteristics of BCI/AR device 402 will be adjusted automatically, or by the patient through a patient controlled mode to maximize bit rate of information transfer by elevating output from the basal forebrain or thalamus to raise a level of vigilance, or adjust basal ganglia outflow to facilitate motor behavior if intact motor output channels remain.

Figure 8:
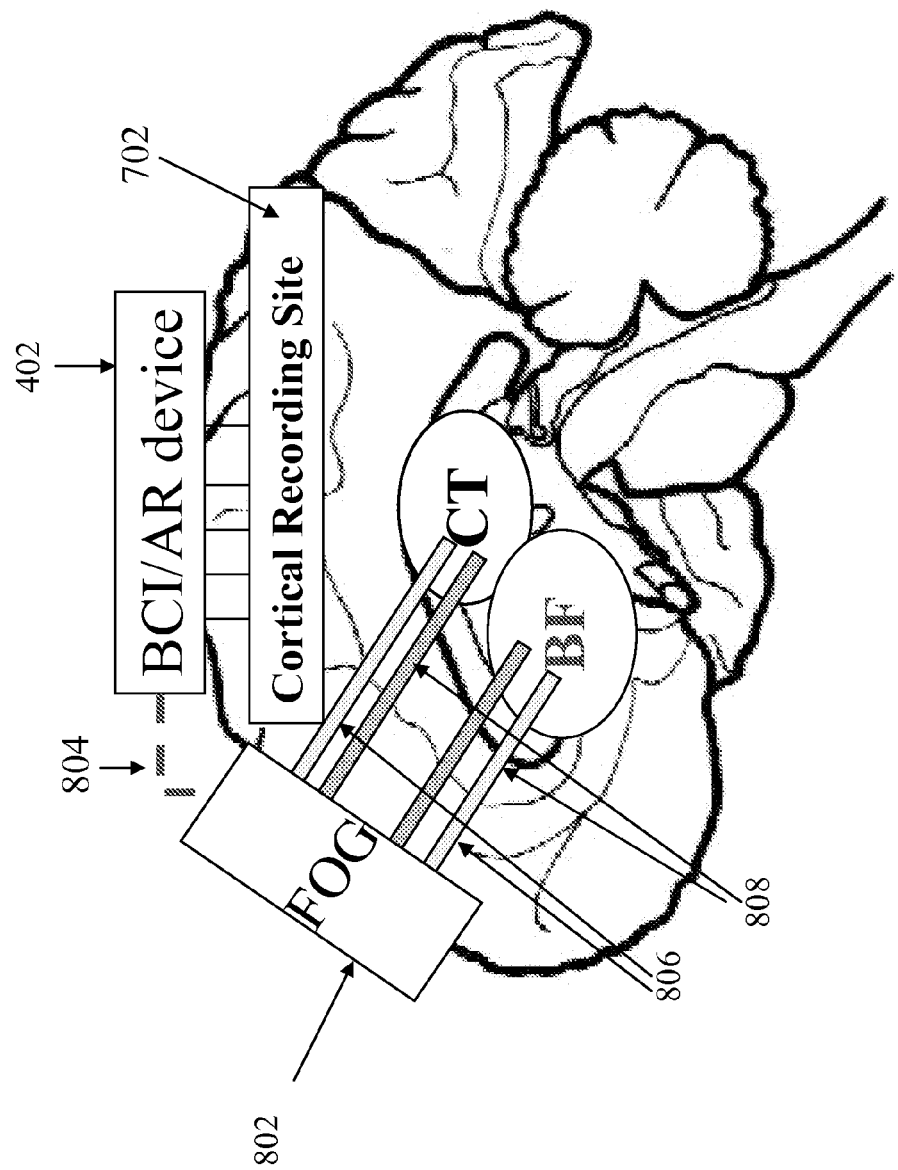
FIG. 8 illustrates a BCI-AR device with a fiber-optogenic (FOG) device to stimulate deep brain structures for maintaining a targeted arousal level, according to another embodiment of the present invention.

FIG. 8 illustrates another embodiment of the present invention where instead of an electrical implantable pulse generator 704 (described in FIG. 7), a fiberoptic-optogenetic (FOG) system 802 is coupled to BCI/AR device 402. In an exemplary scenario, FOG system 802 can be configured to modulate activation of viral transfected cells within the basal forebrain (BF) or central thalamus (CT). In FIG. 8, shaded lines shown as pipes 806, and solid body lines shown as pipes 808, indicate light pipes producing inactivation (e.g., a yellow light for hyperpolarizing currents produced by halorhodopsin channels) or activation (e.g., blue light for channel-rhodopsin inserted channels producing membrane depolarization), respectively. Individual pipes 806 and 808 are fiber-optic cables that can change color and are controlled at the surface by FOG system 802 under feedback control by BCI/AR device 402. FOG system 804 can be coupled to BCI/AR device 402 through direct electric coupling, or RF coupling, or other coupling known to one skilled in the art.

Figure 9:
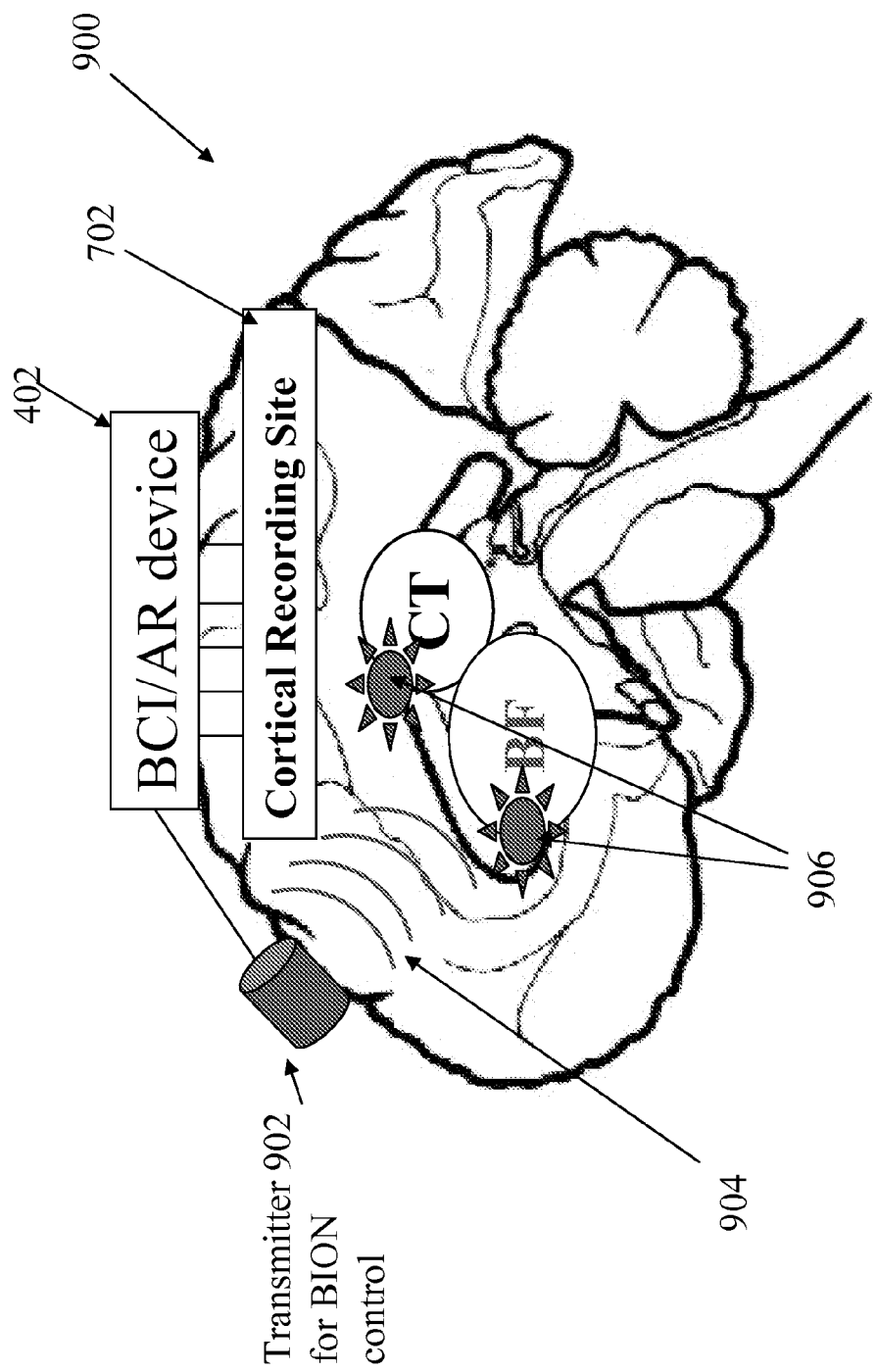
FIG. 9 illustrates a BCI-AR device with a BCI/AR device coupled with a transmitter for Bionic control of deep brain stimulation, according to another embodiment of the present invention.

FIG. 9 illustrates a coupling of BCI/AR device 402 to a BION system 900 is illustrated. BION system 900 comprises a BION transmitter 902 coupled to BCI/AR device 402 for controlling implanted BIONs 906. BION transmitter 902 acts through radiofrequency pulses 904 to control implanted BIONs 906 which show electro-optical properties depending on changes in neuronal activity. Alternatively, BION transmitter 902 can be used to alter neuronal activity to maintain wakeful states of the patient.

It is to be noted that although BCI/AR device 402 is shown to be connected to stimulation systems including one of implantable pulse generator 704, FOG system 802, and BION system 900, in FIGS. 7-9, respectively, a combination of implantable pulse generator 704, FOG system 802, and BION system 900, or a plurality of such systems and device can be used depending upon specific requirements of a patient.

Another aspect of the present invention is directed to a computer readable medium having stored thereon instructions for controlling a Brain Computer Interface (BCI) device, such as BCI/AR device 402, implanted in a selected patient's brain. The computer readable medium comprises machine executable code which when executed by at least one processor, causes the processor to perform a series of steps. Neuronal activity detected by one or more electrodes and sensors 606 is received at the BCI device attached to the selected patient's brain. A communication channel between the patient and an external device controlled by the patient is established. A rate of information passing through the communication channel from the BCI device is measured. A region of the patient's brain involved in arousal regulation is stimulated, in response to the measuring, under conditions effective to adjust the rate of information passing from the BCI device through the communication channel. Such a computing system and computer readable medium is described in more detail in FIG. 10.

Figure 10:
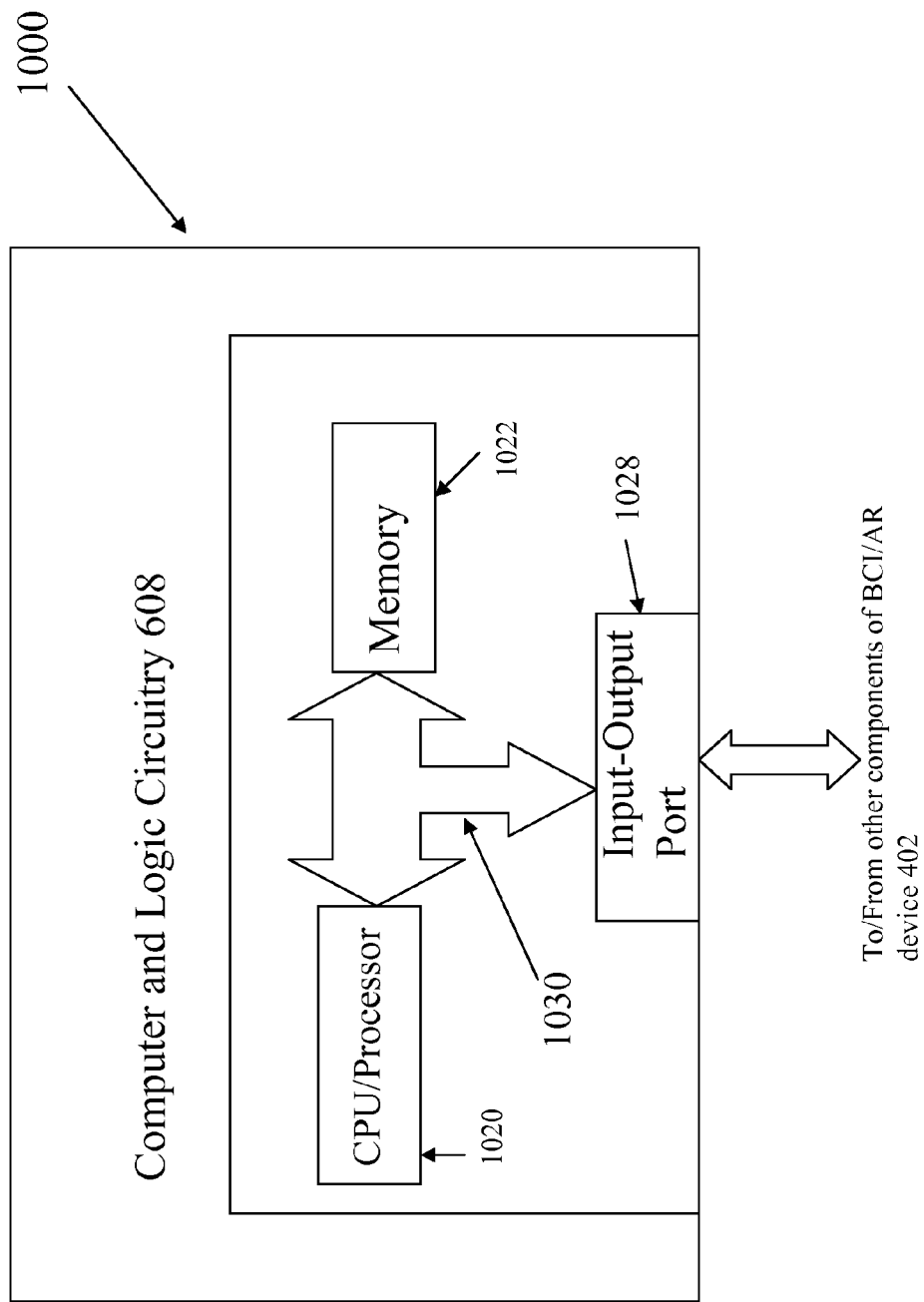
FIG. 10 illustrates an exemplary computer system used for assisting the BCI device in various operations, according to another embodiment of the present invention.

FIG. 10 illustrates a special-purpose computing system 1000 which is a part of the computer and logic circuitry 608 of BCI/AR device 402. Computing system 1000 is configured to process the detected level of neuronal activity in the selected patient's brain, communicate via an input-output port 1028, further over a communication channel, the processed neuronal activity data to I/O interface 612 of BCI/AR device 402 coupled to the patient's brain, and instruct BCI/AR device 402 to generate and send a response stimulus signal to the patient's brain in response to the detected neuronal activity level under conditions effective to adjust the rate of information passing from the BCI device through the communication channel. Computing system 1000 includes a central processing unit ("CPU") or processor 1020, a memory 1022, and input-output port 1028 which are coupled together by a bus 1030 or other link. Computing system 1000 can include other numbers and types of components, parts, devices, systems, and elements in other conventional components.

Processor 1020 executes a computer program or code comprising stored instructions for one or more aspects of the present invention, as described and illustrated herein. In addition, the processor could execute other programmed instructions. Processor 1020 executes code for measuring a rate of information passage through the communication channel from the BCI/AR device 402, and also establishes protocols for communication channels via I/O interface 612. Processor 1020 retrieves information from memory 1022 that stores information about a patient's optimal neuronal activity parameters (e.g., optimal performance range 1302 of FIG. 13), and compares it with measured neuronal activity parameters. According to one embodiment of the present invention, memory 1022 can store neuronal firing rate threshold corresponding to an arousal level of a patient, waveform patterns corresponding to different regions of the brain during arousal, in addition to real time data about neuronal activity detected by electrodes and sensors 606 of BCI/AR device 402. By executing instructions/computer program code stored in memory 1022, processor 1020 computes a binary decision data stream (such as plot 1106 of FIG. 11) after comparing a pre-stored feature vector with feature vector 610 provided by state monitoring module 604 and performance monitoring module 606. Processor 1020 further executes computer code that carries out the steps of determining an optimal information rate and stimulation intensity of the response stimulus signal to be sent by BCI/AR device 402 via its transmission module 650, and controlling an external device based upon the detected neuronal activity, where the external device is electronically interfaced to BCI/AR device 402 and optionally connected to the patient. Processor 1020 can be programmed to transfer computed data regarding a patient's neuronal activity to an external server too.

Memory 1022 stores the programmed instructions written in a computer programming language or software package for carrying out one or more aspects of the present invention as described and illustrated herein, although some or all of the programmed instructions could be stored and/or executed elsewhere. For example, instructions for executing the above-noted steps can be stored in a distributed storage environment where memory 1022 is shared between one or more computing systems similar to computing system 1000. For example, memory 1022 stores a threshold level of neuronal activity firing rate and upon execution of instructions by processor 1020, provides pre-stored values for adjusting rate of information output by BCI/AR device 402, and for computing physical parameters of intensity of the response stimulus signal to be sent to the patient's brain when optimal performance range 1302 is not met or the threshold neuronal firing rate level is not exceeded.

A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to one or more processors, can be used for memory 1022.

Input-output port 1028 is used to operatively couple and communicate between computing system 1000, and other parts of BCI/AR device 402, although other types and numbers of connections and configurations to other types and numbers of systems, devices, and components can be used. For example input-output port 1028 can be programmed to a display or an external device prior to BCI/AR device 402 sending the response stimulus signal if the detected neuronal activity matches a neuronal activity parameter. Alternatively, using input-output port 1028, processor 1020 can repetitively send additional response stimulus signals over the communication channel to the patient's brain until a particular neuronal activity parameter, stored on computer readable memory 1022, is met.

Alternatively, processor 1020 is caused to send a response stimulus signal when the detected level of neuronal activity does not match with a decoded waveform pattern stored on memory 1022. For sending instructions to various components of BCI/AR device 402, processor 1020 communicates via input-output port 1028 to establish a communication channel between the brain and BCI/AR device 402. Processor 1022 can comprise an embedded codec to encode and decode the detected neuronal activity onto a binary data stream representation of the detected neuronal activity. Further, processor 1022 comprises instructions to carry out operations on the detected neuronal activity data with one or more of an electrical, a fiber optic, or a bionic neuron communication channel interfaced with processor 1022.

In an alternative arrangement, processor 1020 is caused to receive a continuous time voltage representation signal to BCI/AR device 402 generated as an output of an electroencephalogram (EEG, described in FIG. 12) or electrocorticogram in response to the detected neuronal activity. Processor 1020 also performs computations related to a spectral analysis of the detected neuronal activity for identifying one or more frequencies associated with the neuronal activity, and modifies the response stimulus signal based upon the identified one or more frequencies. As a result, processor 1020 is used by BCI/AR device 402 for regulating arousal levels to modulate neuronal activity of one or more regions of the brain involved with arousal regulation, and for feedback controlling stimulation of arousal systems of the brain.

Furthermore, processor 1020 is configured to process data associated with monitoring of performance and state of BCI/AR device 402 by collecting neuronal data associated with the detected neuronal activity in the form of one or more of a single-unit neuron activity, local field potentials, or electrocorticogram activity and extracts signal features from the detected neuronal activity to aid performance monitoring module 602 and state monitoring module 604 to form and store in memory 1022, feature vector 610, in addition to one or more pre-stored feature vectors, suitable for computer analysis.

According to another aspect of the invention, BO/AR device 402 uses processor 1020 to activate one or more of the central thalamus, striatum, basal forebrain, and/or brainstem sub-cortical structures in the patient's brain for regulating the arousal level.

Although embodiments of computing system 1000 are described and illustrated herein as completely residing on BCI/AR device 402, computing system 1000 can be implemented on any suitable computing system or computing device. It is to be understood that the devices and systems described herein are for exemplary purposes and many variations of the specific hardware and software are possible, as will be appreciated by those skilled in the relevant art(s).

Alternatively, each of the systems may be conveniently implemented using one or more general purpose computer systems, microprocessors, digital signal processors, and micro-controllers, programmed according to the teachings described and illustrated herein. For example, processor 1020 can be an Intel Core Duo® processor provided by Intel Corporation of Santa Clara, Calif.

In addition, two or more computing systems or devices can be substituted for any one of the systems described above. Accordingly, principles and advantages of distributed processing, such as redundancy and replication, also can be implemented, as desired, to increase the robustness and performance of the devices and systems described above. The embodiments of the present invention may also be implemented on computer system or systems that extend across any suitable network using any suitable interface mechanisms and communications technologies, including, by way of example only, telecommunications in any suitable form (e.g., voice and modem), wireless communications media, wireless communications networks, cellular communications networks, G3 communications networks, Public Switched Telephone Networks (PSTNs), Packet Data Networks (PDNs), the Internet, intranets, and combinations thereof.

Figure 14:
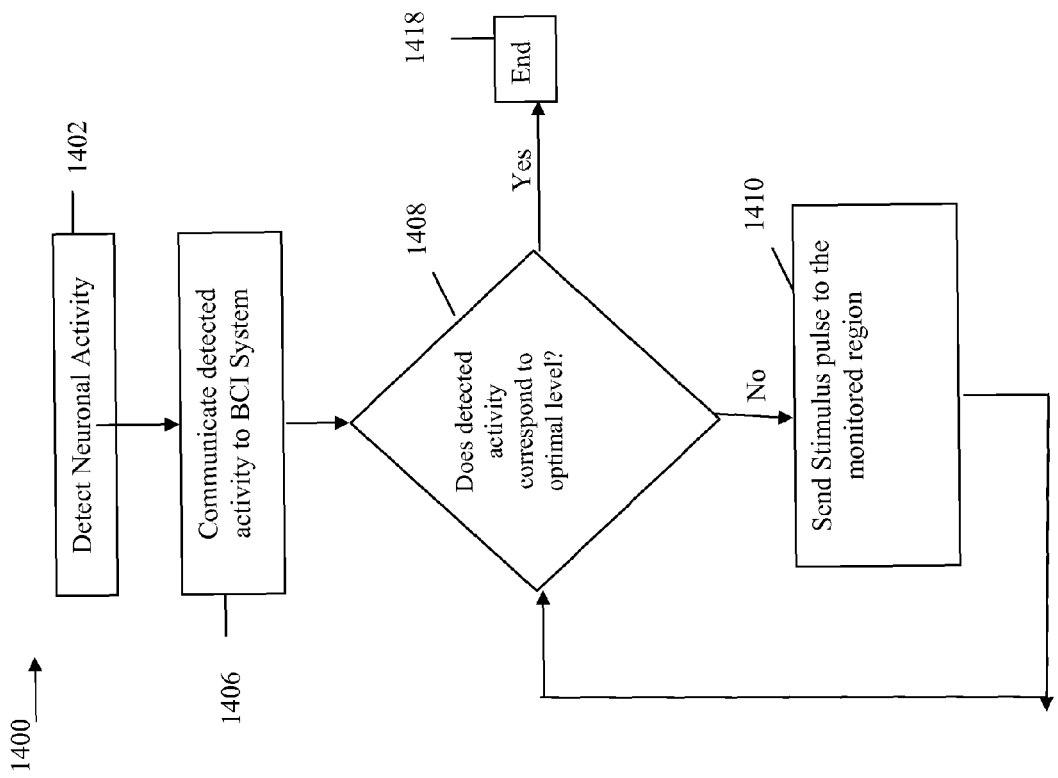
FIG. 14 illustrates a flowchart for determining arousal levels for activation/de-activation of the BCI device, according to various embodiments of the present invention.

The embodiments may also be embodied as a computer readable medium having instructions stored thereon for one or more aspects of the present invention as described and illustrated by way of the embodiments herein, as described herein, which when executed by a processor, cause the processor to carry out the steps necessary to implement the methods of the embodiments, such as steps described and illustrated in flowchart 1400 of FIG. 14.

FIGS. 11-14 provide a detailed description of the steps of transduction of neural activity recorded by BCI/AR device 402 into a control signal for controlling an activation device such as the implantable pulse generator 704 to optimally stimulate one or more of Arousal Regulation components shown in FIGS. 2A-D (AR component).

Figure 11:
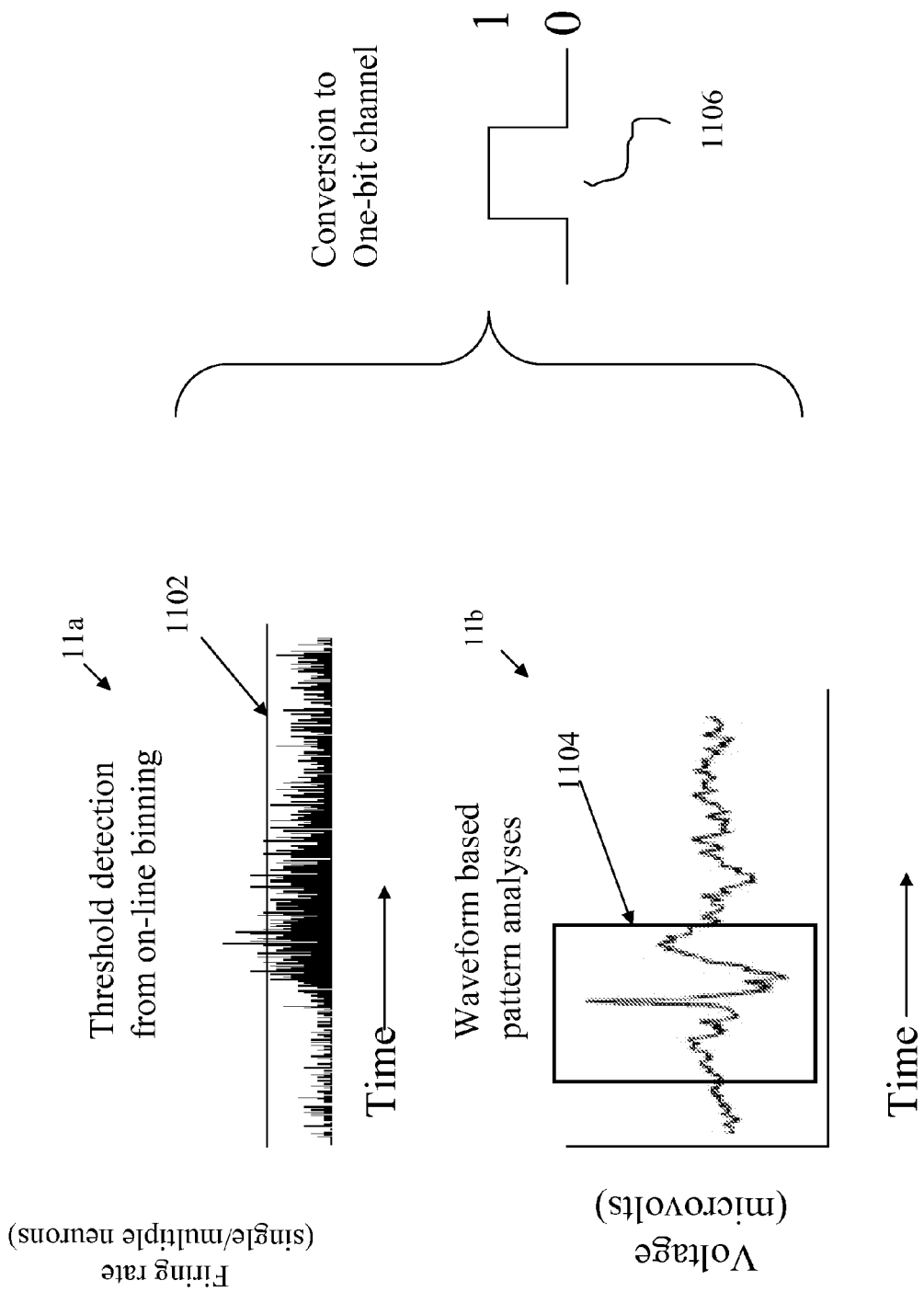
FIG. 11 illustrates an exemplary firing rate threshold detection technique and a waveform based on a pattern analysis technique implemented by the BCI device and the computer system to establish a 'one-bit' communication channel or channels that are monitored within the BCI to determine an information rate (bits/second) in a patient, according to another embodiment of the present invention.

Referring to FIG. 11, plot 11a illustrates two exemplary methods for discrimination of single or multiple neuronal spike recordings. For example, when the neuronal firing rate exceeds a threshold rate 1102, pre-stored in a memory 1022 of computer system 1000 of FIG. 10, BCI/AR device 402, using computer and logic circuitry 608, makes a decision by changing a bit value from a binary '0' to binary '1' to record that a neuronal activity above threshold rate 1102 was detected. Other threshold methods can also be applied to pick a rate of firing of neurons from binned or smoothed estimates of the firing rate. When neuronal firing rates exceed threshold rate 1102, a single bit value is changed from 0 to 1 resulting in a one-bit communication channel as shown by plot 1106 (with an arbitrary time base). This process is continuously repeated and BCI/AR device 402 provides a one-bit communication output from the patient. If the rate of information production drops below a reference range (such as optimal performance range 1302 of FIG. 13) the BCI/AR device 402 sends a signal to, for example, implantable pulse generator 704, to send an electrical stimulus signal to a desired subcortical region of the brain to increase arousal. Alternatively, such a stimulus signal can also be sent via FOG system 802 of FIG. 8 or via Bionic transmitter 902 of FIG. 9, as described above.

Alternatively, FIG. 11 shows in plot 11b another approach that can be used for arousal regulation of a patient using BCI/AR device 402, in addition to the methods described above. In this case, the change of bit value in plot 1106 from a binary '0' to a binary '1' then will depend on a signal detected by the BCI/AR device 402 showing a match between a detected waveform pattern 1104 to a pre-defined waveform stored, for example, in memory 1022 of BO/AR device 402. Waveform pattern 1104 indicates the firing of one or more neurons. Using pre-defined criteria and neuronal activity parameters for firing rate over specific time windows, a response based upon the binary data stream of plot 11a can be generated and sent. This process is continuously repeated and BCI/AR device 402 provides a one-bit communication output from the patient. If the rate of information production drops below a reference range (such as optimal performance range 1302 of FIG. 13) the BCI/AR device 402 sends a signal to, for example, implantable pulse generator 704, to send an electrical stimulus signal to a desired subcortical region of the brain to increase arousal, thereby increasing the rate of information passage through BCI/AR device 402, in a feedback loop. Alternatively, such a stimulus signal can also be sent via FOG system 802 of FIG. 8 or via Bionic transmitter 902 of FIG. 9, as described above.

Figure 12:
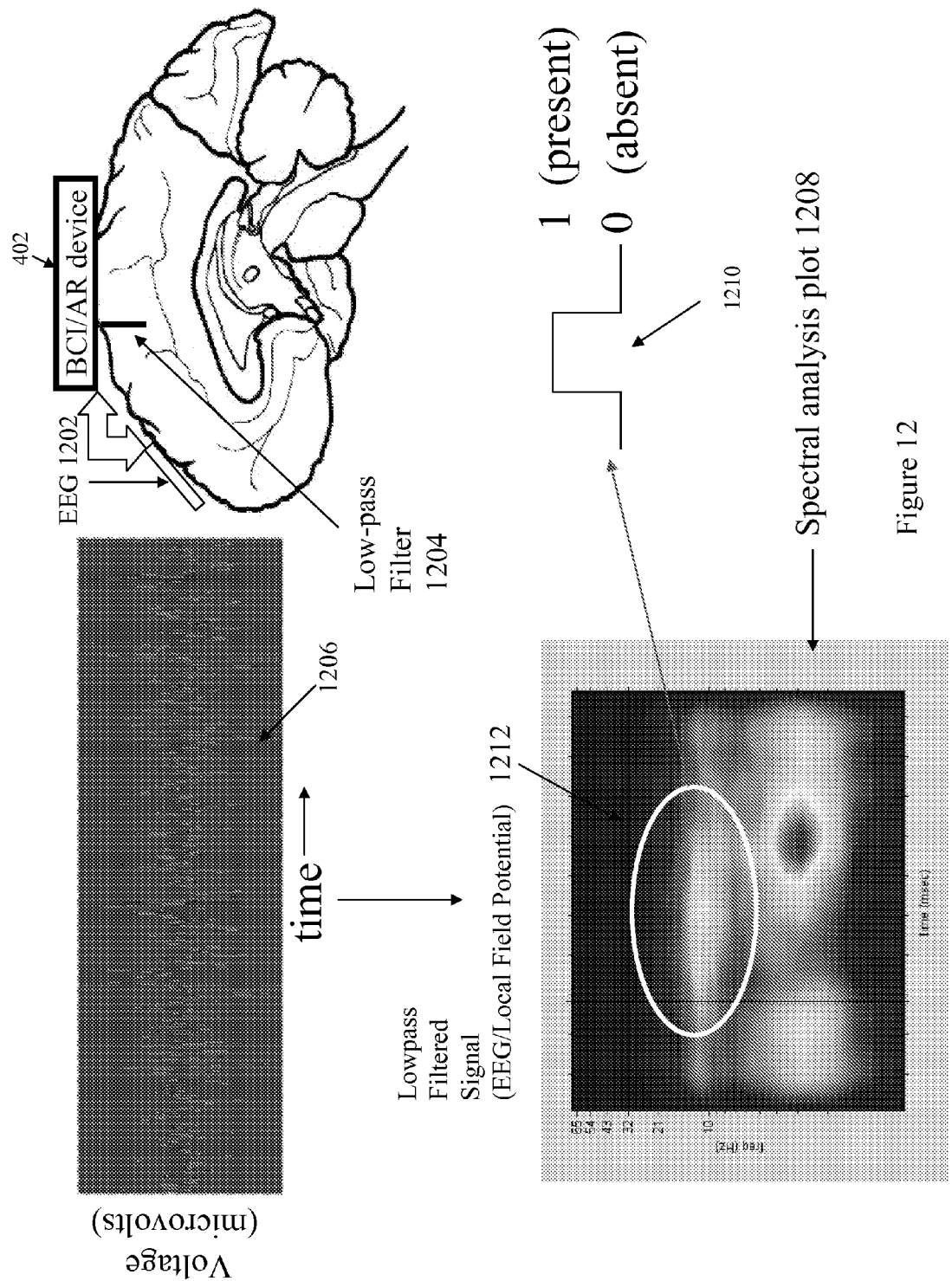
FIG. 12 illustrates an electrocorticogram/electroencephalogram (EEG) attached to a BCI device used to measure arousal state, according to another embodiment of the present invention.

FIG. 12 illustrates an electro-encephalogram (EEG) 1202 connected to BO/AR device 402. BCI/AR device 402 comprises a low pass filter 1204 (for filtering local field potentials) coupled to pass electrical signals of below pre-determined frequency range to pass through, although other types of filters known to one skilled in the art can also be used. EEG 1202 detects neuronal activity as a time-varying voltage (e.g., in micro volts), as shown in plot 1206. A continuous voltage tracing from an EEG 1202 comprising a recording electrode (e.g., placed on or in skull) or a local field potential (LFP) signal recorded from a single-unit recording electrode or dedicated electrode is shown both as time series and converted into its time-varying spectral content using a time-frequency spectral analysis plot 1208. In plot 1208, a circle 1212 identifies, for example, a brief burst of 10 Hz activity seen in the time series and isolated in the time-frequency plane. The presence or absence of strong power in an exemplary frequency band shown by circle 1212 could be used as a one bit channel decision criterion shown in plot 1210 to make a decision of whether or not neuronal activity of specific frequency occurred. Depending upon design of low-pass filter 1204, different frequency bands can be detected and analyzed. Further, plot 1208 illustrating the spectral analysis of a signal detected by EEG 1202 and filtered by low-pass filter 1204 can be generated using a tapered Fourier transform technique. Alternatively, plot 1208 can also be generated using other techniques such as a wavelet transform, fast-Fourier transform, and other spectral extraction techniques known to one skilled in the art. Further, detected neuronal activity can be outputted, for example, on a display 1280 for inspection by other persons, e.g. medical professionals or a doctors, or family members.

Again, spectral plot 1208 can be modified, using feedback techniques, by BCI/AR device 402 so as to result in an optimal performance of BCI/AR device 402. For example, by sending specific pulses at 10 Hz to one or more regions of the brain associated with arousal level regulation, a patient's capability to attain optimal performance range 1302 (shown in FIG. 13) can be enhanced.

Figure 13B:
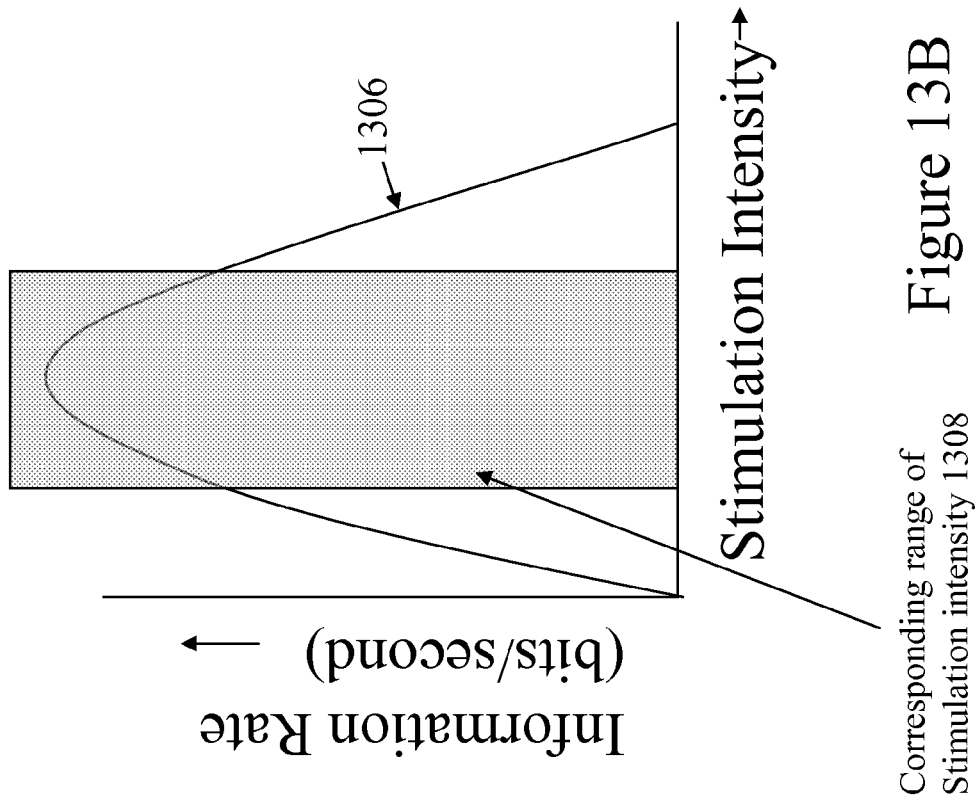
FIGS. 13A-B illustrate an exemplary technique for controlling information rate operated upon by the BCI/AR device and an estimation technique for stimulation intensity of the stimulation pulse used for arousal of the patient, according to another embodiment of the present invention.
Figure 13A:
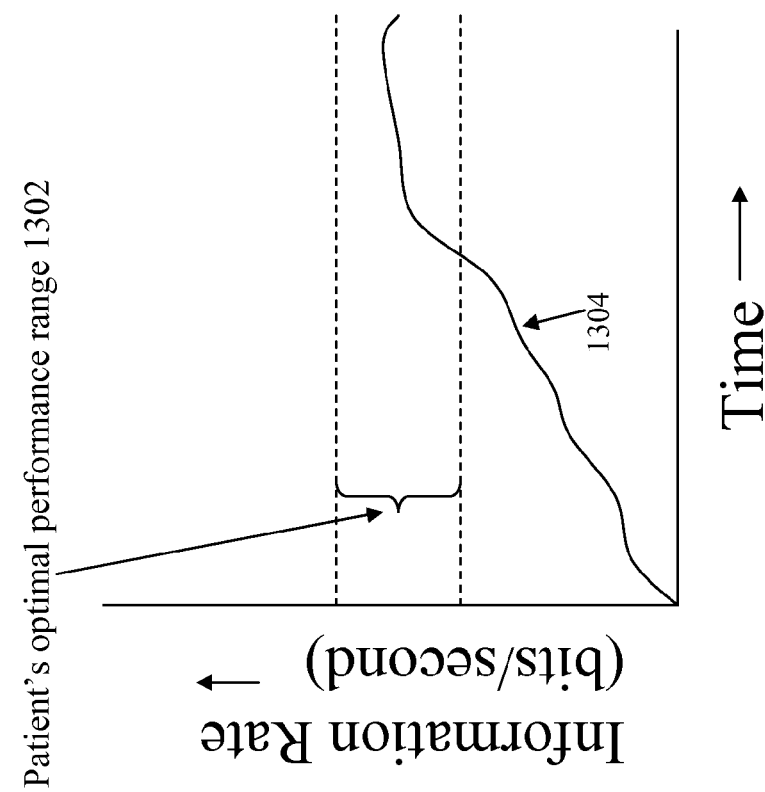

FIGS. 13A and 13B show plot illustrating the control of information rate (e.g., in bits/second) and the intensity level of the stimulation pulse sent by BCI/AR device 402 to stimulate and/or regulate the patient's arousal systems. Information rate (or rate of information passage) through BCI/AR device 402 is measured based upon neuronal activity detected, as described above, for example, in FIG. 6. FIG. 13A illustrates a rate of information output from BCI/AR device 402 as a function of time (in arbitrary units). Output information rate of BCI/AR device 402 is adjusted until such an output information rate matches the patient's own optimal range of performance shown as range 1302 in FIG. 13A. Such an optimal information rate range 1302 also corresponds to optimal response stimulation signal intensity, shown as shaded area 1308 in FIG. 13A. Based upon a determination of whether or not detected neuronal activity is at a pre-defined threshold of information rate and matches the optimal information rate range 1302, BCI/AR device 402 via its transmission module 650 sends as a feedback, an optimal response stimulus signal to maintain a level of stimulation of the cortical/sub-cortical brain regions involved with the arousal systems shown in FIGS. 2A-2D. It is to be noted that such optimal ranges are unique to each patient, and for every new patient selected for a treatment using the present invention, BCI/AR device 402 has to be first trained to "learn" such an optimal range. Such learning by the BCI/AR device 402 can be performed, for example, using neural networks or other machine learning mechanisms, known to one skilled in the art. Alternatively, if the detected neuronal activity level is already within an optimal range for a neuronal activity parameter, such as rate of information shown in plot 1304, associated with the arousal level, BCI/AR device 402 can send signals at an optimal information rate via input-output system 612, prior to stimulating the cortical/sub-cortical regions. Further, such an adjustment of the information rate output by BCI/AR device 402 and corresponding adjustment and sending of stimulation can be performed repetitively until the information rate matches a particular neuronal activity parameter (e.g., patient's optimal range 1302).

BCI/AR device 402 sends the response stimulus signal to the regions of the brain as a feedback by adjusting optimal stimulation intensity 1308 to lie within a peak of an expected inverted "U" curve 1306, as shown in FIG. 13B. Such an adaptive feedback control of rate of information passage from main input/output interface 612 using a corresponding stimulation intensity of stimulation applied to the cortical/sub-cortical structures involved in arousal regulation allows for optimal performance of BCI system 500's output information rate component and maintenance of the performance of the BCI system 500 over time. Control of information rate and stimulation intensity is performed using computer and logic circuitry 608 of the BCI/AR device 402.

According to one aspect of the invention, a method of controlling a BCI/AR device 402 implanted in a patient's brain is disclosed herein. The method comprises selecting a patient with the implanted BCI/AR device 402 configured to receive neuronal activity from one or more electrodes and sensors 606 connected to the patient's brain and to establish a communication channel between the patient and external device 630 controlled by the patient. A rate of information passage through the communication channel (input-output interface 612) from BCI/AR device 402 is measured, and a region of the patient's brain involved in arousal regulation is stimulated, in response to the measuring, under conditions effective to adjust the rate of information passing from BCI/AR device 402 through the main input/output interface 612. Such a method can be carried out using steps of an exemplary flowchart 1400 shown and described in FIG. 14.

FIG. 14 illustrates an exemplary flowchart 1400 for a method of performing the steps described above with respect to BCI/AR device 402. Steps shown in flowchart 1400 are carried out using BCI/AR device 402, more particularly using computer and logic circuitry 608. The flowchart 1400 begins in step 1402, where neuronal activity is detected by electrodes and sensors 606 from a region involved in arousal regulation, or any other region of the brain under monitoring.

The flow then proceeds to step 1406 where the detected neuronal activity is communicated to BCI/AR device 402 via a wired or a wireless communication channel. Such a detected neuronal activity is processed by performance and state monitoring modules 602 and 604, as described above in FIG. 6, for appropriately form feature vector 610. Detected neuronal activity is converted to an equivalent rate of information passage through input-output system 612 of BCI/AR device 402, and processed as described in FIGS. 6, 10 and 13 above.

In step 1408, computer and logic circuitry 608 determines whether or not, the detected neuronal activity is either within optimal range 1302, or above threshold level 1102 or matches a decoded waveform 1104 as shown in FIG. 11b, or is of a specific frequency as shown by the spectral analysis plot 1208 of FIG. 12, corresponding to a wakeful state of the patient. Such a determination is made, for example, based upon a comparison of feature vector 610 with a pre-stored feature vector stored in memory 1022 of computer and logic circuitry 608.

If not, in step 1410, BCI/AR device 402 instructs one of implantable pulse generator 704, FOG system 802, or BION transmitter 902 to send a response stimulation signal/pulse whose characteristics are determined based on plots in FIGS. 13A and 13B, to adjust arousal level. BCI/AR device 402 repetitively performs steps 1408 and 1410 until the patient meets the pre-determined criterion for arousal level neuronal activity parameters. Alternatively, if the detected neuronal activity corresponds to the patient's unique optimal range 1302, rate of information is not adjusted. In such a scenario, an external device can be directly controlled by the BCI/AR device 402 based upon the detected neuronal activity, or the detected neuronal activity can be simply output to an external display 630, or an audio speaker, a cathode-ray tube, or other output devices well known to those skilled in the art.

It should be noted that steps 1402-1418 are shown as an example only and one skilled in the art, after reading this disclosure, can contemplate modifications depending upon specific needs. Steps 1402-1418 can be performed in real time, or in an "off-line" mode. Also, steps 1402-1418 do not have to be performed in the order shown and can be performed in other ways, as can also be contemplated by one skilled in the art after reading this disclosure.

Figure 15:
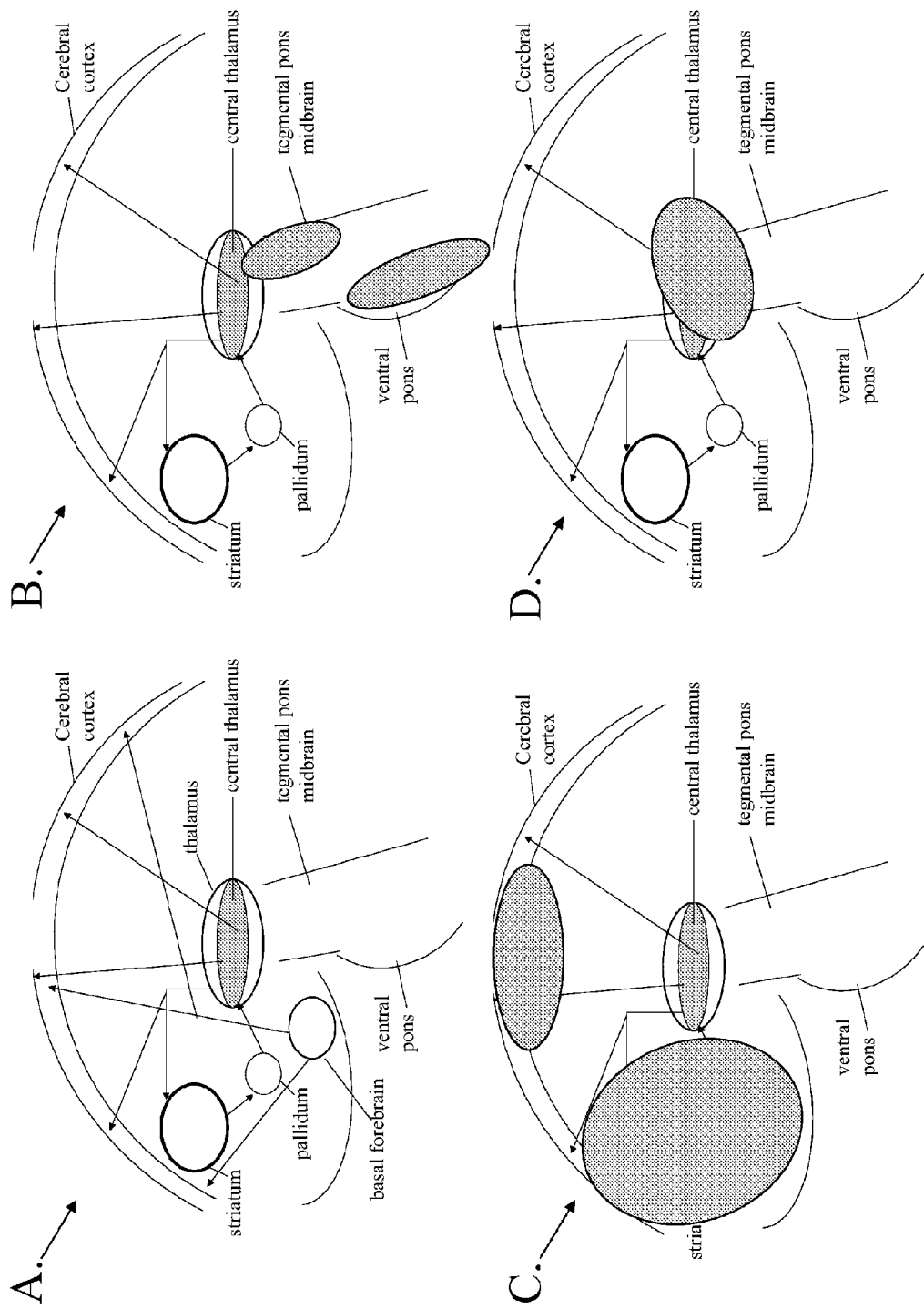
FIGS. 15A-D illustrate exemplary patient conditions in which the present invention can be used.

Since, each patient is unique in terms of the damage incurred to his/her arousal system, various embodiments of the present invention can be used in treatment of complex lesion pattern damages. Some such exemplary lesion patterns that can be advantageously treated using the methods and devices of the present invention are disclosed in FIG. 15. Although many patients with brain-injuries might be helped by a BCI/AR device 402 in principle (e.g., those with post head injury, encephalitis, subarachnoid hemorrhage, and cardiac arrest with dysfunction of the basal ganglia), several common patterns of cerebral injury can be identified for which both injury to the arousal regulation mechanisms of the anterior forebrain including the connections between the thalamus and frontal/prefrontal/premotor cortices (particularly the anterior cingulate, supplementary motor area, premotor cortex, and orbitofrontal and prefrontal cortices), the thalamostriatal projection, the basal forebrain projections to the frontal cortex, and upper tegmental brainstem projections to the thalamus, are combined with direct injury to the motor output systems arising in the motor cortex or basal ganglia and projecting down the spinal column.

FIG. 15A shows several relevant structures of normal anatomy. FIG. 15B shows one large group of patients that may typically require the combined techniques of the BCI/AR device 402. This group corresponds to patients who have survived a basilar artery thrombosis. Such a lesion and similar forms of injury such as hemorrhages or infections within the upper brainstem may produce a combination of ventral pontine damage in association with injury to the tegmental pons and midbrain regions damaging ascending arousal projections to the thalamus and basal forebrain. Often these latter injuries include damage to the thalamic intralaminar system and upper midbrain reticular regions that support activation of the frontal executive and basal ganglia systems. As a result of such injuries, patients may slowly recover an unstable wakeful state of consciousness, retaining normal or near-normal cognitive function that is fragile in the face of mild intercurrent stress (sleep deprivation, infection, etc). When combined with injury to the ventral pons that damages the majority of descending motor pathways, it may be nearly impossible or impossible for these patients to signal response through the motor system.

FIG. 15C shows another common pattern of injury associated with aneurysmal rupture in the anterior forebrain within the region of the anterior communicating cerebral artery or anterior cerebral arteries that may damage frontal/prefrontal/premotor cortical regions, striatum, basal forebrain, or thalamocortical radiating fibers. Additional damage to the motor pathways may arise from these initial injuries or involvement of other arterial vessels in a process called vasospasm that leads to strokes within the motor outflow pathway.

FIG. 15D shows another possible pattern of injury involving motor pathway fibers within the internal capsule (e.g., diffuse axonal injury) and concomitant bilateral damage to the central thalamus due to compression of Percheron's artery during an early stage of brain swelling. Patients with lesion patterns as delineated in FIGS. 15B-D may be inappropriately diagnosed as in vegetative or minimally conscious state yet are closer to normal function and potentially able to communicate. The present invention provides a system and method of maintaining internal levels of arousal through the patient's own brain controlled adjustment of activity level via BCI/AR system 402 that both controls the activation of subcortical systems downregulated by loss of ascending inputs and use of the same system to control communication with the outside world and external devices such as motor prosthetics.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A Brain Computer Interface (BCI) system comprising:
   one or more sensors configured to detect neuronal activity of one or more cortical or subcortical neuronal populations involved in arousal regulation of a selected patient's brain;
   a state monitoring module coupled to the one or more sensors, configured to store and process a first set of variables associated with a state of the detected neuronal activity;
   a performance monitoring module coupled to the one or more sensors, configured to store and process a second set of variables associated with an information rate of the detected neuronal activity, and configured to output the information to an output device via a communication channel; and
   a processing module coupled to the state monitoring module and the performance monitoring module, configured to extract a feature vector based upon the processed first and second set of variables, and configured to stimulate, in response to the detected neuronal activity, a region of the patient's brain involved in arousal regulation under conditions effective to adjust the output of information through the communication channel.

2. The BCI system of claim 1, wherein the one or more sensors are coupled to at least one of an implantable pulse generator via a pair of electrodes, a fiber-optogenic (FOG) system, and a Bionic transmitter.

3. The BCI system of claim 2, wherein the FOG system comprises fiber optic cables controlled by the FOG system.

4. The BCI system of claim 2, wherein the Bionic transmitter communicates with bionic neurons implanted in cortical or subcortical neuronal populations over a radio frequency channel to provide neuronal activity signals to the one or more sensors.

5. The BCI system of claim 1, wherein the one or more sensors are remote sensors.

6. The BCI system of claim 1 further comprising:
   a filter coupled to the one or more sensors, the state monitoring module, and the performance monitoring module, configured to eliminate background noise from the detected neuronal activity.

7. The BCI system of claim 6, wherein the filter is at least one of a low-pass filter, a band-pass filter, and/or a notch filter.

8. The BCI system of claim 1 further comprising:
   a display system coupled to a communication interface and configured to display at least one of a time-series representation of the detected neuronal activity obtained directly from the one or more sensors, a spectral analysis of the detected neuronal activity, and/or a matched waveform unique to the patient corresponding to the detected neuronal activity.

9. The BCI system of claim 1, wherein the first set of variables comprise at least one of background signal data, low-pass filter output data, sensor activity data, and/or a firing rate of one or more neurons in one or more cortical or subcortical neuronal populations of the patient's brain.

10. The BCI system of claim 1, wherein the second set of variables comprise an intensity level corresponding to the information rate of the detected neuronal activity.

11. The BCI system of claim 1, wherein the processing module is configured to control an external device based upon the detected neuronal activity.

12. The BCI system of claim 1, wherein the detected neuronal activity is generated by a thought process of the selected patient.

13. The BCI system of claim 1 further comprising:
   a cortical recording memory device configured to sample neuronal activity corresponding to at least one of single-unit activity, local field potentials, and electrocorticogram/electroencephalogram activity and
   a decoder for decoding the detected neuronal activity received over a communication channel interface within the BCI.

14. A method comprising:
   selecting a patient coupled to a BCI system comprising:
      one or more sensors configured to detect neuronal activity of one or more cortical or subcortical neuronal populations involved in arousal regulation of the selected patient's brain;
      a state monitoring module coupled to the one or more sensors, configured to store and process a first set of variables associated with a state of the detected neuronal activity;
      a performance monitoring module coupled to the one or more sensors, configured to store and process a second set of variables associated with an information rate of the detected neuronal activity, and configured to output the information to an output device via a communication channel; and
      a processing module coupled to the state monitoring module and the performance monitoring module, configured to extract a feature vector based upon the processed first and second set of variables, and configured to stimulate, in response to the detected neuronal activity, a region of the patient's brain involved in arousal regulation under conditions effective to adjust the output of information through the communication channel;
   detecting neuronal activity of one or more cortical or subcortical neuronal populations involved in arousal regulation of the selected patient's brain with the one or more sensors;

storing and processing, with the state monitoring module coupled to the one or more sensors, the first set of variables associated with the state of the detected neuronal activity;

storing and processing, with the performance monitoring module coupled to the one or more sensors, the second set of variables associated with the information rate of the detected neuronal activity, and outputting the information to the output device via the communication channel; and extracting, with the processing module coupled to the state monitoring module and the performance monitoring module, the feature vector based upon the processed first and second set of variables, and stimulating, in response to the detected neuronal activity, the region of the patient's brain involved in arousal regulation under conditions effective to adjust the information to the output device through the communication channel.

15. The method of claim 14, wherein the BCI system further comprises a filter coupled to the one or more sensors, the state monitoring module, and the performance monitoring module, and the method further comprises:

eliminating, with the filter, background noise from the detected neuronal activity.

16. The method of claim 14, wherein the BCI system further comprises a display system coupled to a communication interface and the method further comprises:

displaying, with the display system, at least one of a time-series representation of the detected neuronal activity obtained directly from the one or more sensors, a spectral analysis of the detected neuronal activity, and/or a matched waveform unique to the patient corresponding to the detected neuronal activity.

17. The method of claim 14, wherein the processing module is configured to control an external device based upon the detected neuronal activity and the method further comprises controlling the external device with the processing module based on the detected neuronal activity.

18. The method of claim 17, wherein said controlling occurs if the detected neuronal activity level is within an optimal range for a neuronal activity parameter associated with an arousal level with the arousal level being measured by detecting the neuronal activity level of the region involved in arousal regulation.

19. The method of claim 14, wherein the BCI system further comprises a cortical recording memory device and a decoder, said method further comprising:

sampling, with the cortical recording memory device, a neuronal activity corresponding to at least one of single-unit activity, local field potentials, and electrocorticogram/electroencephalogram activity, and decoding, with the decoder, the detected neuronal activity received over a communication channel interface within the BCI.

20. The method of claim 14 further comprising:

repetitively stimulating the patient's brain to adjust the rate of information and to adjust a particular neuronal activity level parameter.

21. The method of claim 14, wherein the selected patient has substantially absent motor pathways, a motor pathway impairment, motor control impairment, a lack of vigilance arousal maintenance, a brain injury due to a stroke or a trauma, encephalitis, a subarachnoid hemorrhage, a brain stem hemorrhage, a brain stem infection, a basilar artery thrombosis, a thrombosis cardiac arrest, a hypoxia, nutritional deficiencies, a degenerative illness, neoplastic diseases, infectious diseases, or complications thereof.

22. The method of claim 14, wherein said stimulating is carried out with at least one of an electrical, a fiber optic, or a bionic neuron stimulation system.

23. The method of claim 14, wherein said stimulating is carried out with a deep brain stimulator device coupled to the BCI system.

24. The method of claim 14 further comprising:

performing a spectral analysis of the detected neuronal activity for identifying one or more frequencies associated with the received neuronal activity, wherein said stimulating is modified based upon the identified one or more frequencies.

25. The method of claim 14, wherein the detected neuronal activity is associated with an arousal level of a deep brain neuronal population.

26. The method of claim 14, wherein said stimulating comprises:

adjusting a stimulation intensity level of a response stimulus signal sent to the region of the patient's brain involved in arousal regulation to match the patient's optimal information rate and stimulation intensity.

27. The method of claim 14, wherein said stimulating comprises:

activating at least one of the central thalamus, striatum, basal forebrain, and/or brainstem cortical or sub-cortical structures in the patient's brain.

* * * * *